US012697052B2

(12) United States Patent
Margiott et al.

(10) Patent No.: US 12,697,052 B2
(45) Date of Patent: Aug. 4, 2026

(54) DETACHMENT AND REPLACEMENT METHOD FOR A LAPAROSCOPIC TUBE FOR AN OXIMETRY PROBE

(71) Applicant: ViOptix, Inc., Newark, CA (US)

(72) Inventors: Alex Michael Margiott, Dunbarton, NH (US); Sean Gossin, Media, PA (US); Timothy Lee Sauder, San Francisco, CA (US); Kevin Dunk, Casto Valley, CA (US); Scott E. Coleridge, New York, NY (US); Mark Lonsinger, San Jose, CA (US)

(73) Assignee: ViOptix, Inc., Newark, CA (US)

( * ) Notice: Subject to any disclaimer, the term of this patent is extended or adjusted under 35 U.S.C. 154(b) by 0 days.

(21) Appl. No.: 19/012,833

(22) Filed: Jan. 7, 2025

(65) Prior Publication Data

US 2025/0318760 A1     Oct. 16, 2025

Related U.S. Application Data

(60) Provisional application No. 63/618,864, filed on Jan. 8, 2024.

(51) Int. Cl.
*A61B 5/1455*          (2006.01)

(52) U.S. Cl.
CPC ...... *A61B 5/14552* (2013.01); *A61B 2562/12* (2013.01); *A61B 2562/146* (2013.01)

(58) Field of Classification Search
CPC ............ A61B 5/14552; A61B 1/00126; G02B 23/2469; G02B 6/38
See application file for complete search history.

(56) References Cited

U.S. PATENT DOCUMENTS

| | | | |
|---|---|---|---|
| 9,579,051 B1 * | 2/2017 | Mao ...................... | G02B 6/3885 |
| 10,133,013 B2 * | 11/2018 | Sanandajifar ........... | G02B 6/00 |
| 12,336,817 B2 * | 6/2025 | Bechtel ................ | A61B 5/0205 |
| 2007/0106119 A1 * | 5/2007 | Hirata ................ | G02B 23/2423 |
| | | | 600/179 |
| 2007/0162095 A1 * | 7/2007 | Kimmel ................ | A61B 1/042 |
| | | | 600/172 |
| 2008/0281157 A1 * | 11/2008 | Miyagi .............. | A61B 1/00128 |
| | | | 385/75 |
| 2011/0077473 A1 * | 3/2011 | Lisogurski ............. | G16H 40/63 |
| | | | 600/300 |
| 2011/0184244 A1 * | 7/2011 | Kagaya .............. | A61B 1/00117 |
| | | | 600/182 |

(Continued)

*Primary Examiner* — Michael W Hotchkiss
(74) *Attorney, Agent, or Firm* — Aka Chan LLP

(57)          ABSTRACT

A laparoscopic medical device includes an oximeter sensor at its tip, which allows for making oxygen saturation measurements laparoscopically. The laparoscopic medical device includes a probe unit and a laparoscopic tube that detachably connects with the probe unit so that the laparoscopic tube can be replaced for different patient surgeries and the probe unit can be reused. The probe unit includes a number of optical fibers and the detachable laparoscopic tube includes a number of optical fibers where tips of the fibers of the probe unit and laparoscopic tube connect end to end. Cores of the transmitting optical fibers have smaller numerical apertures and smaller diameters than cores of the receiving optical fibers to facilitate a high percentage of light transmission even when the optical fibers are misaligned at their contacting ends.

32 Claims, 21 Drawing Sheets

(56)         References Cited

U.S. PATENT DOCUMENTS

| | | | |
|---|---|---|---|
| 2011/0224518 A1* | 9/2011 | Tindi ..................... | A61B 5/742 |
| | | | 600/407 |
| 2013/0035550 A1* | 2/2013 | Watanabe .......... | G02B 23/2484 |
| | | | 600/132 |
| 2016/0089001 A1* | 3/2016 | Hara .................. | A61B 1/00029 |
| | | | 600/109 |
| 2016/0282604 A1* | 9/2016 | Yoshino ............. | G02B 23/2453 |
| 2017/0254964 A1* | 9/2017 | Yajima ................ | G02B 6/3878 |
| 2018/0014759 A1* | 1/2018 | Bechtel ............. | A61B 1/00181 |
| 2018/0239124 A1* | 8/2018 | Naruse .................. | G02B 23/26 |

* cited by examiner

214

214a

270d

214b

214c

270b

270c

270

270a

276

276a

276c 275c        275b

275

275a

275d 214a
270a 275a
276a

DETACHMENT AND REPLACEMENT METHOD FOR A LAPAROSCOPIC TUBE FOR AN OXIMETRY PROBE

CROSS-REFERENCE TO RELATED APPLICATIONS

This application claims the benefit of U.S. patent application 63/618,864, filed Jan. 8, 2024, which is incorporated by reference along with all other references cited in this application.

BACKGROUND OF THE INVENTION

The invention generally relates to optical systems that monitor oxygen levels in tissue. More specifically, the invention relates to optical probes, such as laparoscopic oximeters, that include source structures and detector structures in a laparoscopic probe.

Oximeters are medical devices used to measure the oxygen saturation of tissue in humans and living things for various purposes. For example, oximeters are used for medical and diagnostic purposes in hospitals and other medical facilities (e.g., surgery, patient monitoring, or ambulance or other mobile monitoring for, e.g., hypoxia); sports and athletics purposes at a sports arena (e.g., professional athlete monitoring); personal or at-home monitoring of individuals (e.g., general health monitoring, or personal training for a marathon); and veterinary purposes (e.g., animal monitoring).

Pulse oximeters and tissue oximeters are two types of oximeters that operate on different principles. A pulse oximeter uses a patient's pulse to make measurements. A pulse oximeter typically measures the absorbance of light due to pulsing arterial blood. In contrast, a tissue oximeter does not need a pulse in order to function and can be used to make oxygen saturation measurements of a tissue flap that has been disconnected from a blood supply or of tissue, such as internal organs that are connected to a blood supply.

Human tissue, as an example, includes a variety of light-absorbing molecules referred to as chromophores. Such chromophores in the interior tissue of a body include oxygenated hemoglobin, deoxygenated hemoglobin, water, lipid, and cytochrome. Oxygenated hemoglobin and deoxygenated hemoglobin are the most dominant chromophores in interior tissue for much of the visible and near-infrared spectral range. Light absorption differs significantly for oxygenated and deoxygenated hemoglobins at certain wavelengths of light. Tissue oximeters can measure oxygen levels in human tissue by exploiting these light-absorption differences.

Despite the success of existing oximeters, there is a continuing desire to improve oximeters by, for example, improving form factor; improving measurement accuracy; reducing measurement time; lowering cost; reducing size, weight, or form factor, such as for portability; reducing power consumption; and for other reasons, and any combination of these measurements.

In particular, assessing a patient's oxygenation state, at both the regional and local level, is important as it is an indicator of the state of the patient's local tissue health. Thus, oximeters are often used in clinical settings, such as during surgery and recovery, where it may be suspected that the patient's tissue oxygenation state is unstable. For example, during surgery, oximeters should be able to quickly deliver accurate oxygen saturation measurements under a variety of nonideal conditions. While existing oximeters have been sufficient for postoperative tissue monitoring where absolute accuracy is not critical and trending data alone is sufficient, accuracy is, however, important during surgery in which spot-checking can be used to determine whether tissue might remain viable, such as for transplant, or whether a portion of a piece of tissue needs to be removed because the portion might be suspect for becoming necrotic.

Therefore, there is a need for improved tissue oximeter probes and methods of making measurements using these probes.

BRIEF SUMMARY OF THE INVENTION

A laparoscopic medical device includes an oximeter sensor at its tip, which allows the making of oxygen saturation measurements laparoscopically. The laparoscopic medical device includes a probe unit and a laparoscopic tube that detachably connects with the probe unit so that the laparoscopic tube can be replaced for different patient surgeries and the probe unit can be reused. Replaceable laparoscopic tubes facilitate efficient sterility for patient surgeries and a reusable probe unit facilitates cost savings and ecological conservation for a probe unit that includes costly circuitry.

The laparoscopic tube includes a communication tag, such as a near field communication (NFC) tag, that stores calibration information for the optical elements, such as optical fibers, housed by the tube. The probe unit includes a communication tag reader, such as an NFC tag reader, that can retrieve the stored calibration information from the NFC tag. The probe unit includes a memory that stores calibration information. Stored calibration information is used by the processor of the medical device to calibrate generated oximetry information when the medical device is used. In an embodiment, a memory in the laparoscopic tube is electrically connected to the probe unit so that information in the memory can be read and used by the probe unit. The information stored in the memory can be the same information that is stored in the communication tag, such as calibration information, an identifier, an expiration date, other information, or any combination of this information.

Other objects, features, and advantages of the present invention will become apparent upon consideration of the following detailed description and the accompanying drawings, in which like reference designations represent like features throughout the figures.

DETAILED DESCRIPTION OF THE INVENTION

Figure 1:
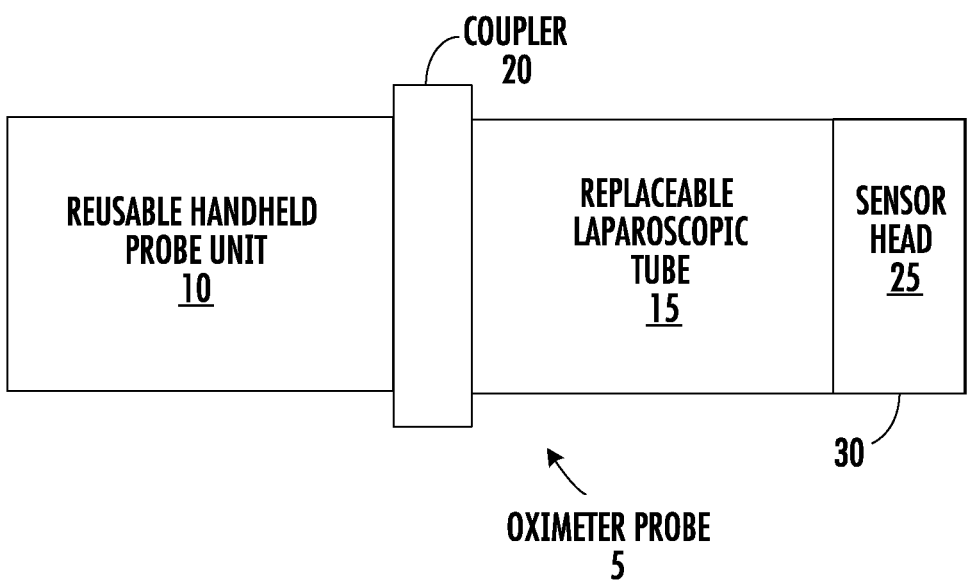
FIG. 1 shows an image of an oximeter probe, in an implementation.

FIG. 1 shows an image of an oximeter probe 5, in an implementation. Oximeter probe 5 is configured to make tissue oximetry measurements of tissue, such as internal tissue, intraoperatively. Oximeter probe 5 may be a handheld device that includes a probe unit 10 and a laparoscopic tube 15 extending from the probe unit. A sensor head 25 is located at a tip portion 30 of the laparoscopic tube. The probe unit is coupled to the laparoscopic tube by a coupler 20. Coupler 20 allows the probe unit 10 and laparoscopic tube 15 to be coupled and decoupled so that a laparoscopic tube can be replaced by a new laparoscopic tube and so that the probe unit can be reused. The probe unit is sometimes referred to as a durable unit because this unit is reusable, whereas the laparoscopic tube is sometimes referred to as a disposable unit because it is to be disposed of after use on a patient. In an implementation, oximeter probe 5 is a disposable probe.

The probe unit may include a number of elements that are relatively costly. Configuring the oximeter probe for reuse of the probe unit allows for cost-saving and ecological conservation. The oximeter probe is fully self-contained and does not need to be connected to another device to be fully operational, in an implementation. That is, the oximeter probe does not need to be wire connected or wirelessly connected to another device to operate. In an implementation, the oximeter probe does connect to other devices, such as one or more other medical devices, a computer system, a display, these devices or systems, or other devices or systems.

In an implementation, the laparoscopic tube of the oximeter probe is adapted for intraoperative use in a patient and can be introduced into the abdominal cavity of the patient through a trocar. An outer surface of the laparoscopic tube can be smooth so that the laparoscopic tube can slide through the trocar smoothly, can rotate within the trocar smoothly, and can slide into contact and past patient tissue smoothly and without abrading the tissue. The oximetry probe can be used on various internal tissues to determine various oximetry information for the tissue. The tissue under test can include intestinal tissue, such as the large intestine, small intestine, tissue that supports these tissues, such as the mesentery tissue, muscle, the liver, kidneys, or other internal tissue.

Figure 2A:
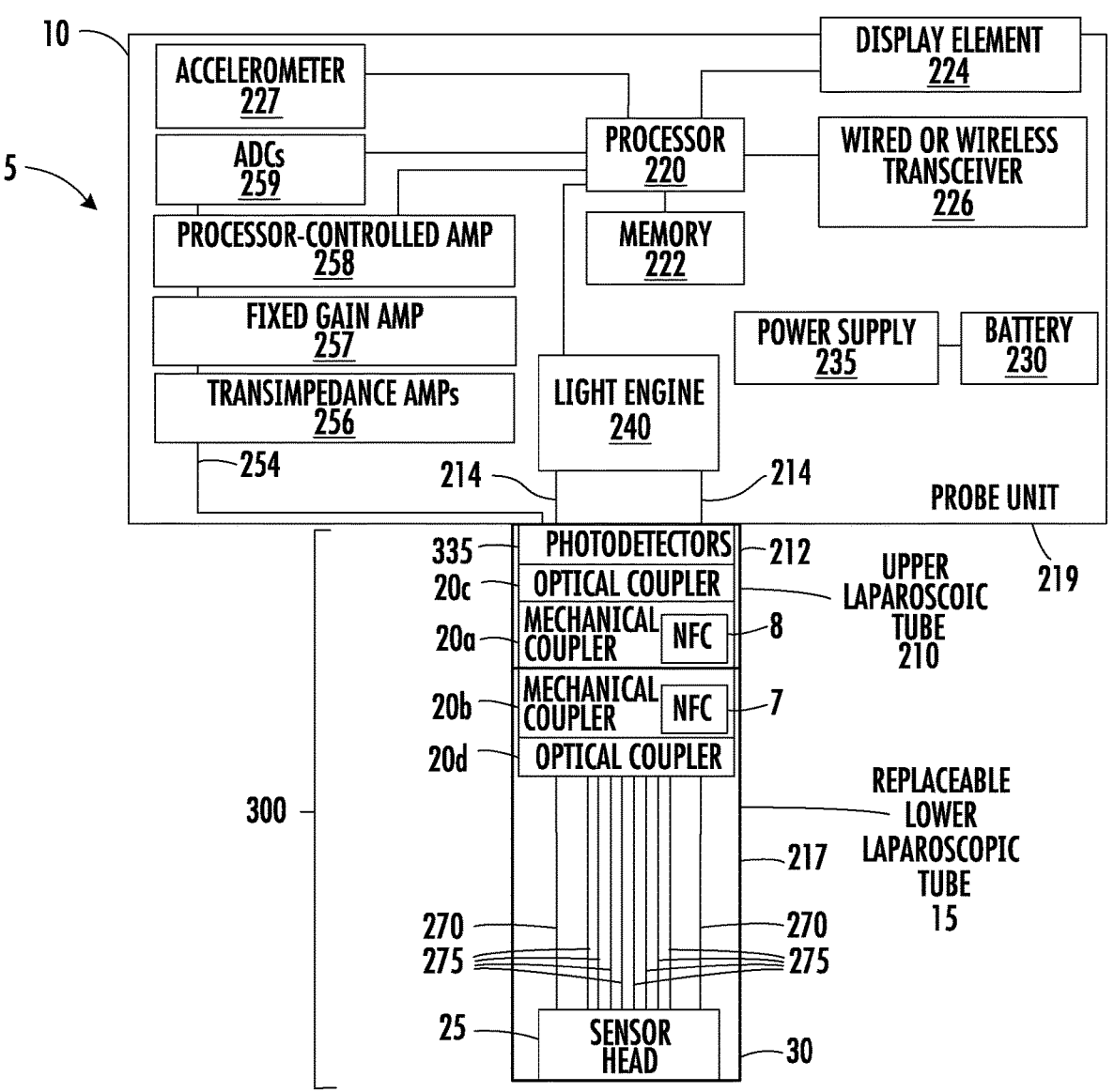
FIGS. 2A-2D are block diagrams of an oximeter probe, in various implementations.

FIG. 2A is a diagram of oximeter probe 5, in an implementation. The probe unit 10 of the oximeter probe 5 includes a housing 219 that houses a processor 220, a memory 222, a display 224, a transceiver 226, an accelerometer 227, a battery 230, a power supply circuit 235, a light engine 240, one or more transimpedance amplifiers (TIAs) 256, one or more fixed gain amplifiers 257, one or more processor-controlled amplifiers 258, one or more analog-to-digital converters (ADCs) 259, one or more electrical conductors 254 (e.g., wires in a cable, such as a flex cable, or electrical traces formed in a printed circuit board), one or more source waveguides 214, other elements, or one or more of these elements in any combination. In an implementation where the probe unit includes display 224, the display element is visible from an exterior of the housing.

The battery is connected to the power supply circuit, which is connected and supplies battery power to the processor, memory, display, transceiver, accelerometer, light engine, the one or more amplifiers, and the one or more analog-to-digital converters. The power supply circuit can be a DC-to-DC (direct current to direct current) converter circuit that converts the voltage output from the battery to a different voltage. The battery of the probe unit can include one or more of a variety of battery types, such as one or more disposable batteries or one or more rechargeable batteries. Disposable batteries are discarded after their stored charge is expended. Some disposable battery chemistry technologies include non-rechargeable lithium ion, alkaline, zinc carbon, or silver oxide. The battery has sufficient stored charge to allow the use of the handheld device for several hours.

In implementations where the battery is rechargeable, the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via a wireless charging system (e.g., a wireless charging system operating according to the Qi standard or another charging standard), via an AC adapter with a cord that connects to the handheld unit. The circuitry in the display can include a recharger circuit (not shown).

The processor is connected to the memory, display, transceiver, accelerometer, light engine, the ADCs, and the one or more amplifiers. The ADCs are connected between the amplifiers and the processor. The amplifiers may be the TIAs, the fixed gain amplifier, the processor-controlled amplifier, or any of these amplifiers in any combination.

In the implementation shown in FIG. 2A, for example, the transimpedance amplifier 256 is connected to photodetectors 335 (described further below) via one or more of the electrical conductors 254. The fixed gain amplifier is connected to both the transimpedance amplifier and the processor-controlled amplifier and is connected between the transimpedance amplifier and the processor-controlled amplifier. The processor-controlled amplifier is connected to the processor for processor-controlled amplification of the voltage amplification by the processor. The processor-controlled amplifier is also connected to the ADCs.

Figure 2B:
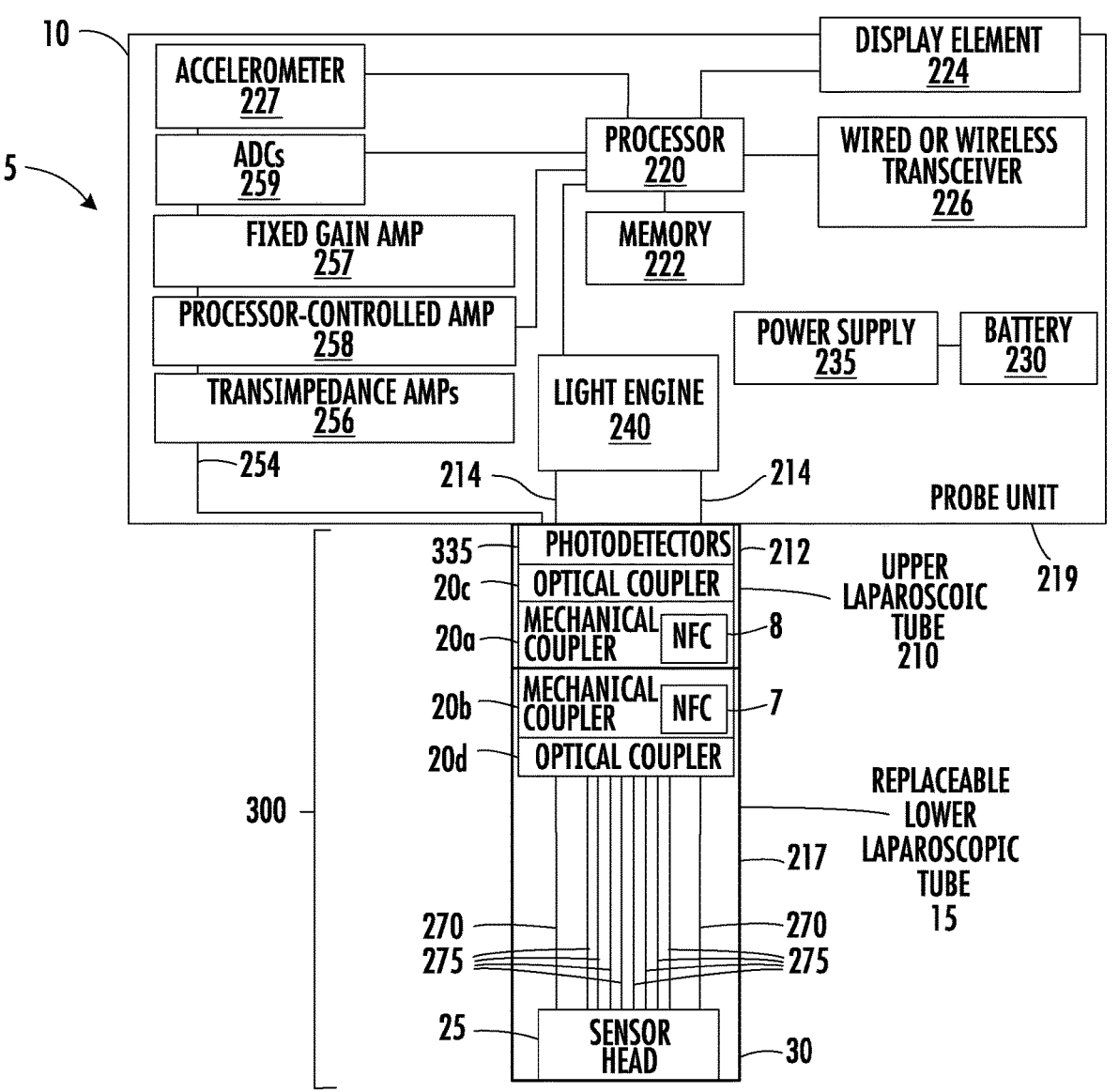

In an implementation shown in FIG. 2B, for example, the transimpedance amplifier 256 is connected to the photodetector 335 via the one or more electrical conductors 254. The processor-controlled amplifier is connected to both the transimpedance amplifier and the fixed gain amplifier and is connected between the transimpedance amplifier and the fixed gain amplifier. The processor-controlled amplifier is also connected to the processor for processor control of the voltage amplification of this amplifier. The fixed gain amplifier is connected to the ADCs.

The TIAs may amplify a low current signal generated by the photodetectors to a stable voltage signal. The fixed gain amplifier may amplify the voltage output from the TIAs to a higher voltage. The processor-controlled amplifier may amplify the higher voltage output by the fixed gain amplifier to a voltage usable by the ADC.

The light engine is electrically connected to the processor and the processor controls the generation of light by the light engine for emission of the light, such as emission into patient tissue or a tissue proxy when the probe unit is used. The light engine includes one or more sources that generate and transmit light, such as visible light, infrared light, or both. Each source can include one or more light emitting diodes (LEDs), such as one, two, three, four, five, six, seven, eight, nine, ten, or more LEDs. Each LED is adapted to emit one or more wavelengths of light, such as visible light, infrared light, or both. The LEDs can be discrete LEDs, organic LEDs (OLEDs), high brightness LEDs (HLEDs), quantum dot LEDs, laser diodes, or other types of LEDs.

The LEDs are optically connected to the first ends of one or more source waveguides 214. The LEDs can be optically connected to the first ends of the one or more source waveguides inside of housing 219. Second ends of the source waveguides are connected to a first optical coupler 20c of the probe unit. In an implementation, the first optical coupler includes a number of apertures formed in the coupler and portions of the second ends of the source waveguides are located in the apertures. Tip portions of the second ends of the source waveguides can extend from the apertures so that the second ends extend outside of the apertures. The tip portions are the terminal ends of the source waveguides.

The source waveguides can be optical fibers or other light guiding elements. One, two, three, four, five, or more LEDs can be optically connected to one or more source waveguides 214. The one or more source waveguides can include 1, 2, 3, 4, 5, 6, 7, 8, 9, 10, or more waveguides.

Probe unit 10 includes an upper laparoscopic tube 210, which extends from housing 219 of the probe unit. The upper laparoscopic tube includes a housing 212, a communication tag reader 8, a first mechanical coupler 20a, the first optical coupler 20c, the one or more photodetectors 335, other elements, or any combination of these elements.

Housing 212 includes an exterior wall and an interior space formed by the exterior wall. The communication tag reader 8, the first mechanical coupler 20a, the first optical coupler 20c, the one or more photodetectors 335, other elements, or any combination of these elements are located in the interior space of housing 212.

Other elements of the probe unit can also be located in the interior space of housing 212 including portions of the one or more conductors 254, portions of the one or more source waveguides 214, portions of both the one or more conductors 254 and the one or more source waveguides 214, or not include portions of the one or more conductors 254 and the one or more source waveguides 214.

Housing 212 of the upper laparoscopic tube 210 is connected to housing 219. Housing 212 can be integrally formed with housing 219, can be fixed to housing 212 (e.g., adhered to the housing, such as by epoxy resin), or can be separable from housing 219. Further, optical coupler 20c can be integrally formed with housing 212.

The communication tag reader can be coupled to the first mechanical coupler so that the tag reader is near an end of the upper laparoscopic tube. The end of the upper laparoscopic tube is distally located with respect to housing 219 of the probe unit. The communication tag reader can be a radio frequency identification tag reader, such as a near field communication (NFC) tag reader.

First mechanical coupler 20a forms a portion of housing 212 and includes one or more coupling devices that are housed in the interior space of housing 212, formed on an exterior surface of housing 212, extend from the interior space to the exterior of the housing, or includes any one or more of these devices in any combination. The mechanical coupler can be accessible from an exterior of the housing.

Replaceable lower laparoscopic tube 15 includes a housing 217, a communication tag 7, a second mechanical coupler 20b, a second optical coupler 20d, one or more detector waveguides 270, one or more source waveguides 275, and the sensor head 25. Housing 217 includes a wall having in interior spaced formed by the wall. The optical coupler, waveguides (e.g., optical fibers), and sensor head are housed in an interior space of the housing of laparoscopic tube 15.

Detector waveguides 270 can include optical fibers or other types of waveguides. The number of optical fibers included in the detector waveguides can be 1, 2, 3, 4, 5, 6, 7, 8, 9, 10 or more. First ends of the detector waveguides are coupled to the second optical coupler 20d and second ends of the detector waveguides are coupled to the sensor head. Source waveguides 275 can include optical fibers or other types of waveguides. The number of optical fibers included in the source waveguides can be 1, 2, 3, 4, 5, 6, 7, 8, 9, 10, 11, 12, 13, 14 or more. The number of optical fibers of the source waveguides is larger than the number of optical fibers of the detector waveguides. First ends of the source waveguides are coupled to the second optical coupler 20d and second ends of the detector waveguides are coupled to the sensor head.

In an implementation, the second optical coupler includes a number of apertures formed in the coupler. Portions of the first ends of the source waveguides and first ends of the detector waveguides are located in the apertures. Tip portions of the first ends of the source and detector can extend from the apertures so that the tip ends extend outside of the apertures. The tip portions are the terminal ends of the source and detector waveguides.

The sensor head includes a number of apertures formed in the sensor head. Portions of the second ends of the source waveguides and second ends of the detector waveguides are located in the apertures. Tip portions of the second ends of the source waveguides and tip portions of the second ends of the detector waveguides can be flush with the openings of the apertures or can be located inside of the apertures.

The sensor head is located inside the tip portion 30 of housing 217 of the laparoscopic tube 15 or can extend from the tip portion 30 of the housing. In an implementation, the sensor head is integrally formed with the housing. In an implementation, the sensor head is not integrally formed with the housing. The source waveguides can emit light from and sensor head and the detector waveguides can receive light at the sensor head.

Communication tag 7 can be coupled to the mechanical coupler so that the communication tag is near an end of the lower laparoscopic tube. Communication tag 7 and communication tag reader 8 are relatively near to each other so that the tag and tag reader can communicate when the upper and lower laparoscopic tubes are connected together by the first and second mechanical couplers. Communication tag 7 can be a radio frequency communication tag, such as a near field communication (NFC) tag. Communication tag reader 8 can be a radio frequency communication tag, such as a near field communication (NFC) tag reader. The communication tag can include a memory that stores information that can be read by the communication tag reader.

In an implementation, second mechanical coupler 20b forms a portion of housing 217 and includes one or more coupling devices that are housed in the interior space of housing 217, formed on an exterior surface of housing 217, that extends from the interior space to the exterior of the housing, or includes any one or more of these devices in any combination. The first and second mechanical couplers 20a-20b are adapted to couple and decouple so that the upper laparoscopic tube 210 and lower laparoscopic tube 15 can be coupled and decoupled. First and second mechanical couplers 20a-20b can include one or more coupler types, including screw mechanism, spring couplers (e.g., spring-loaded F connectors), threaded couplers (e.g., N connector also referred to as a threaded BNC connector), mechanical latches, magnetic couplers, pins and slots (retractable pins that are spring loaded to push the pins out from a pushed in configuration) and apertures, openings, or both to receive the pins (e.g., BNC connectors or C connectors), other couplers, or combinations of these connectors such as threaded connectors that also include pin and slots.

One or both of first and second mechanical couplers 20a-20b can be keyed so that the mechanical couplers mate and couple in one orientation with respect to each other.

Figure 2C:
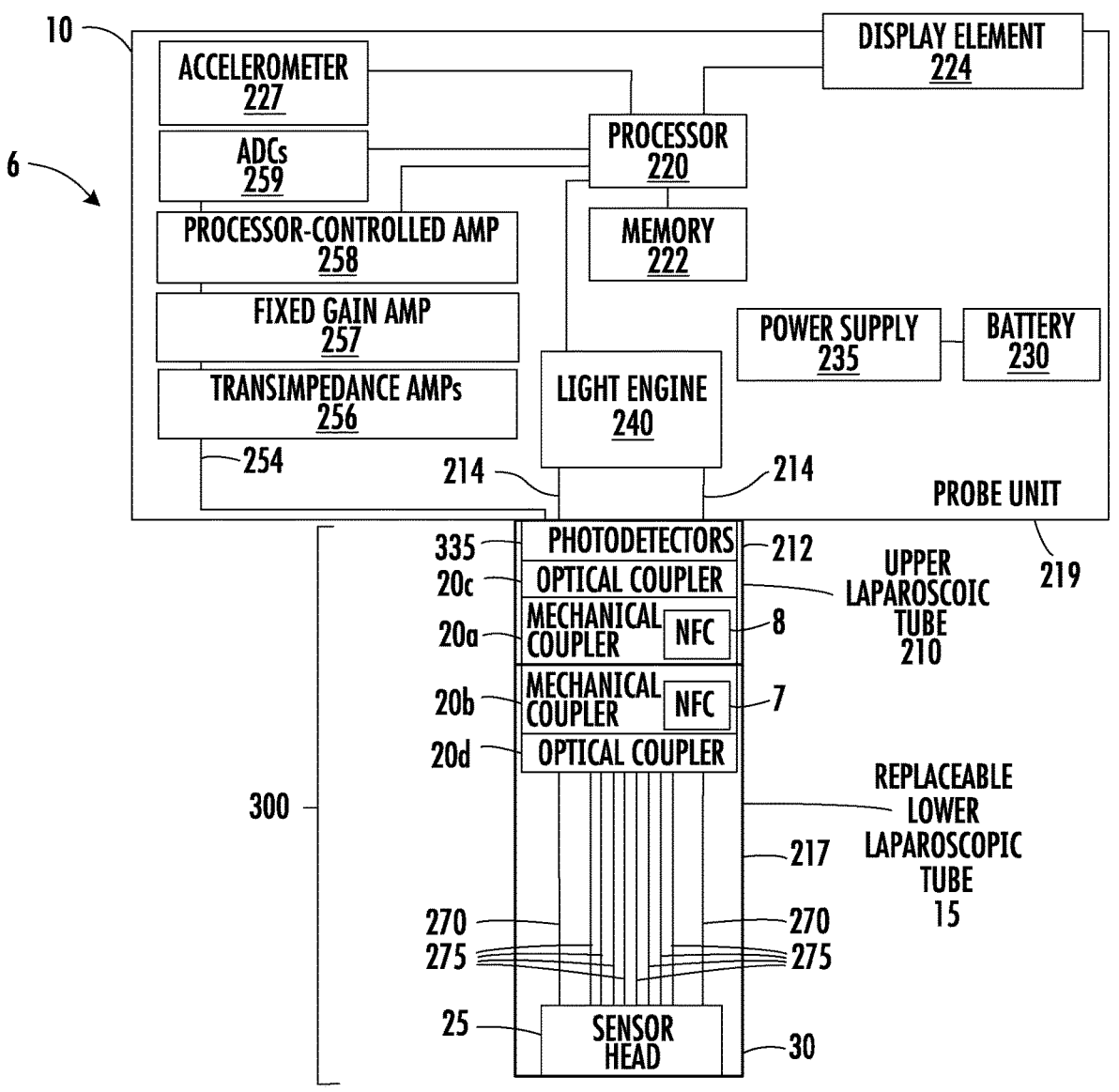
Figure 2D:
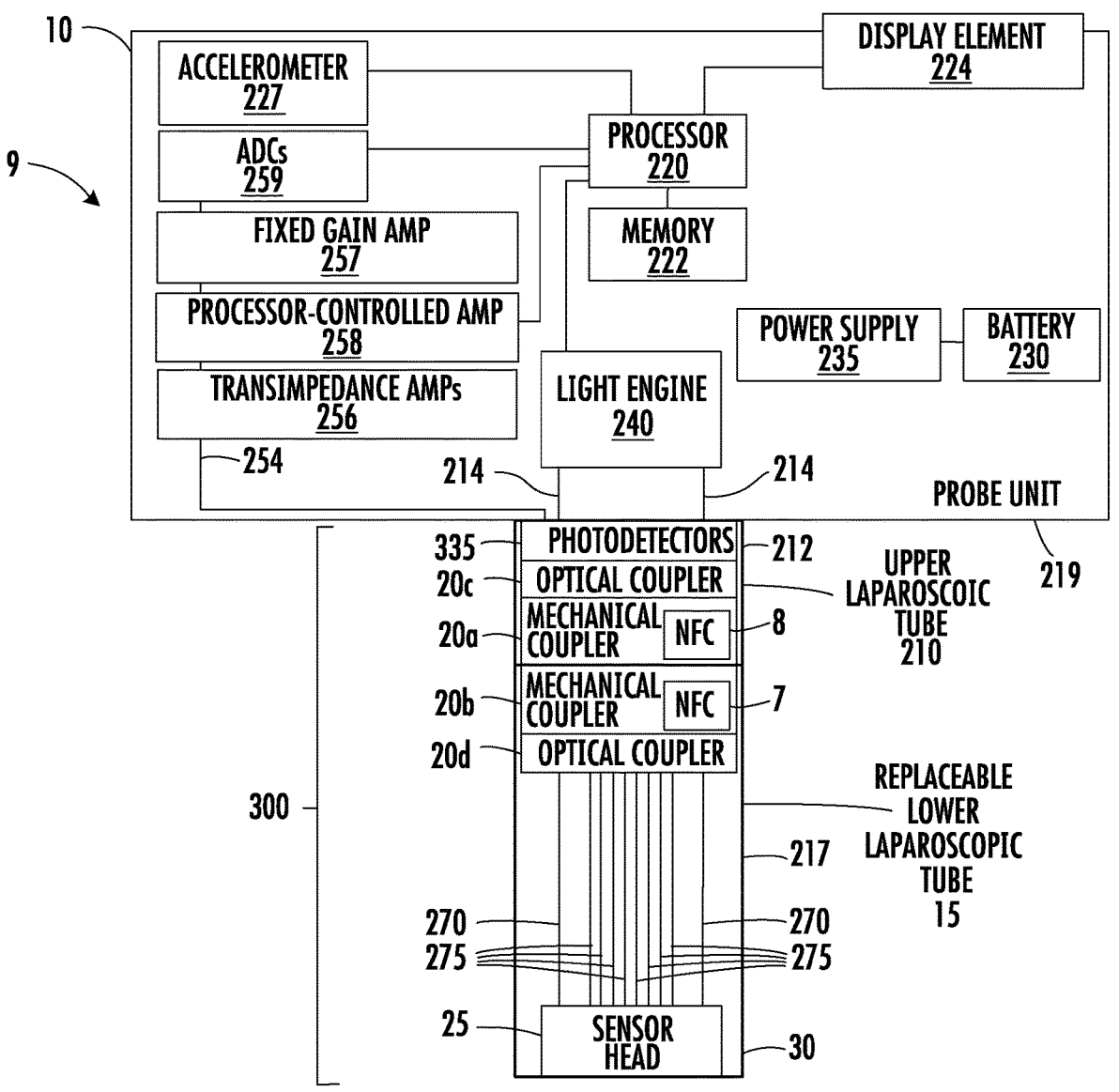

FIG. 2C shows an oximeter probe 6, in an implementation. Oximeter probe 6 differs from oximeter probe 5 shown in FIG. 2A and described above in that oximeter probe 6 does not include a wired or wireless transceiver. FIG. 2D shows an oximeter probe 9, in an implementation. Oximeter probe 9 differs from oximeter probe 5 shown in FIG. 2B and described above in that oximeter probe 9 does not include a wired or wireless transceiver.

Figure 3A:
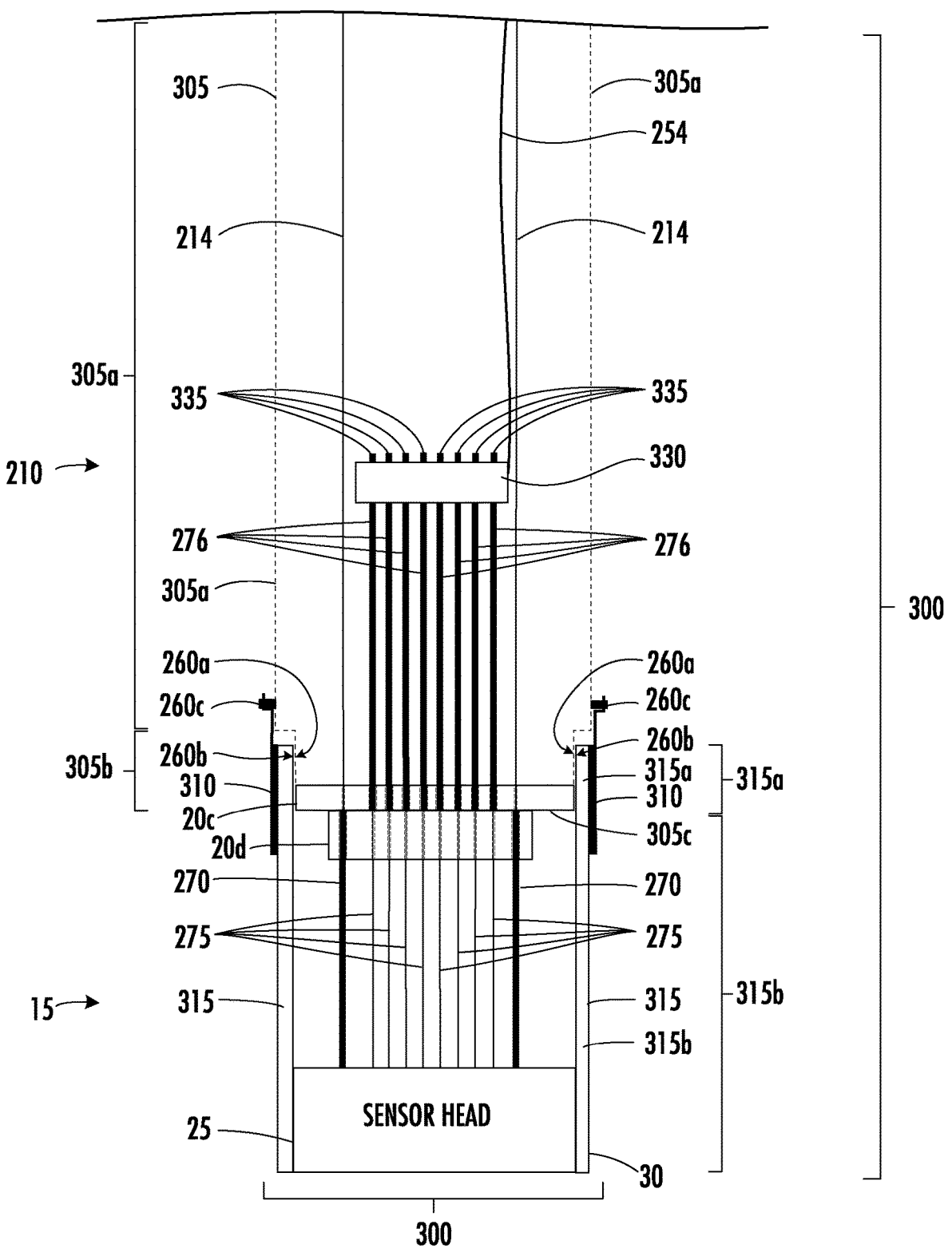
FIGS. 3A-3D show a portion of the upper laparoscopic tube and the lower laparoscopic tube.
Figure 3B:
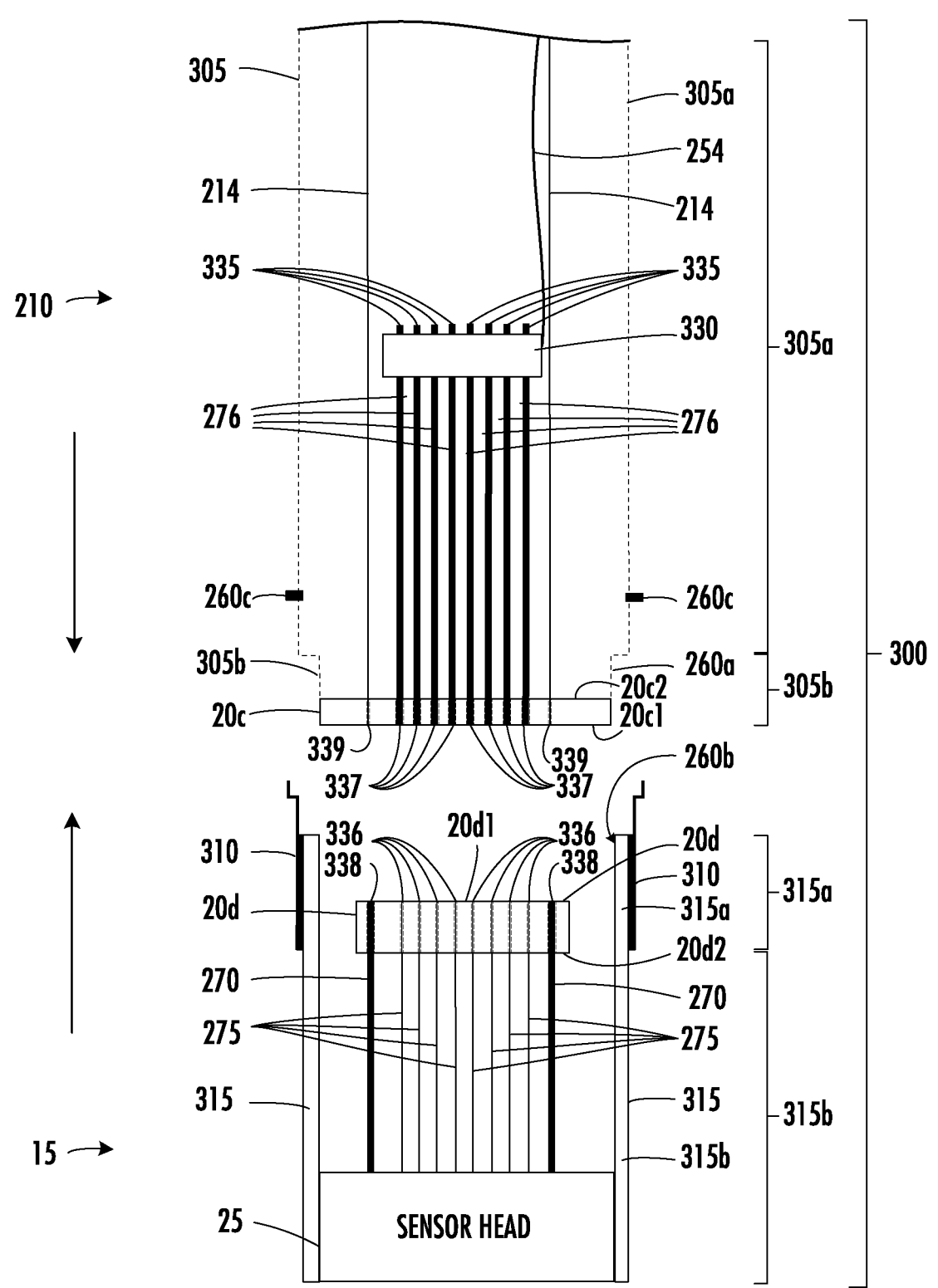
Figure 3C:
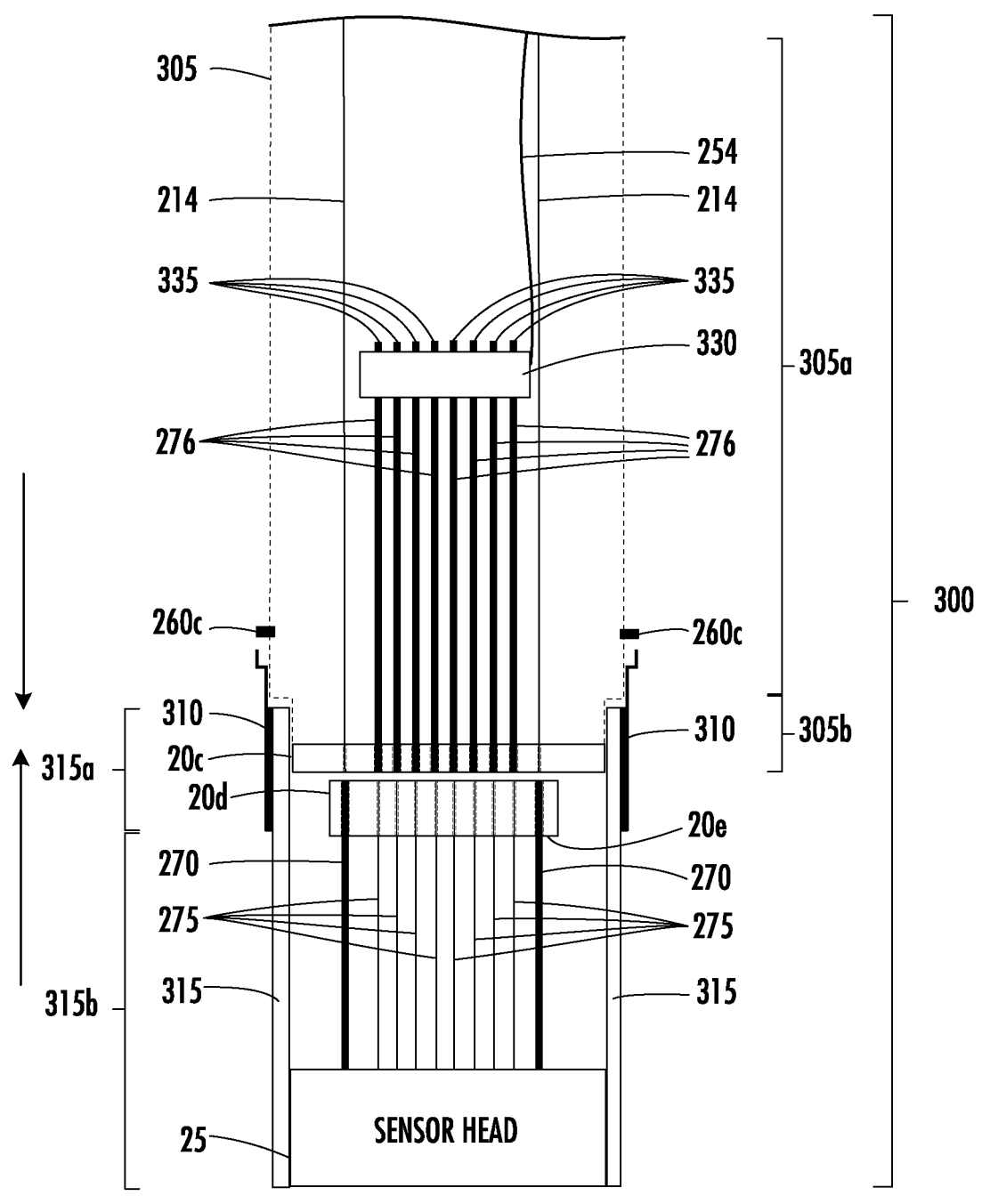
Figure 3D:
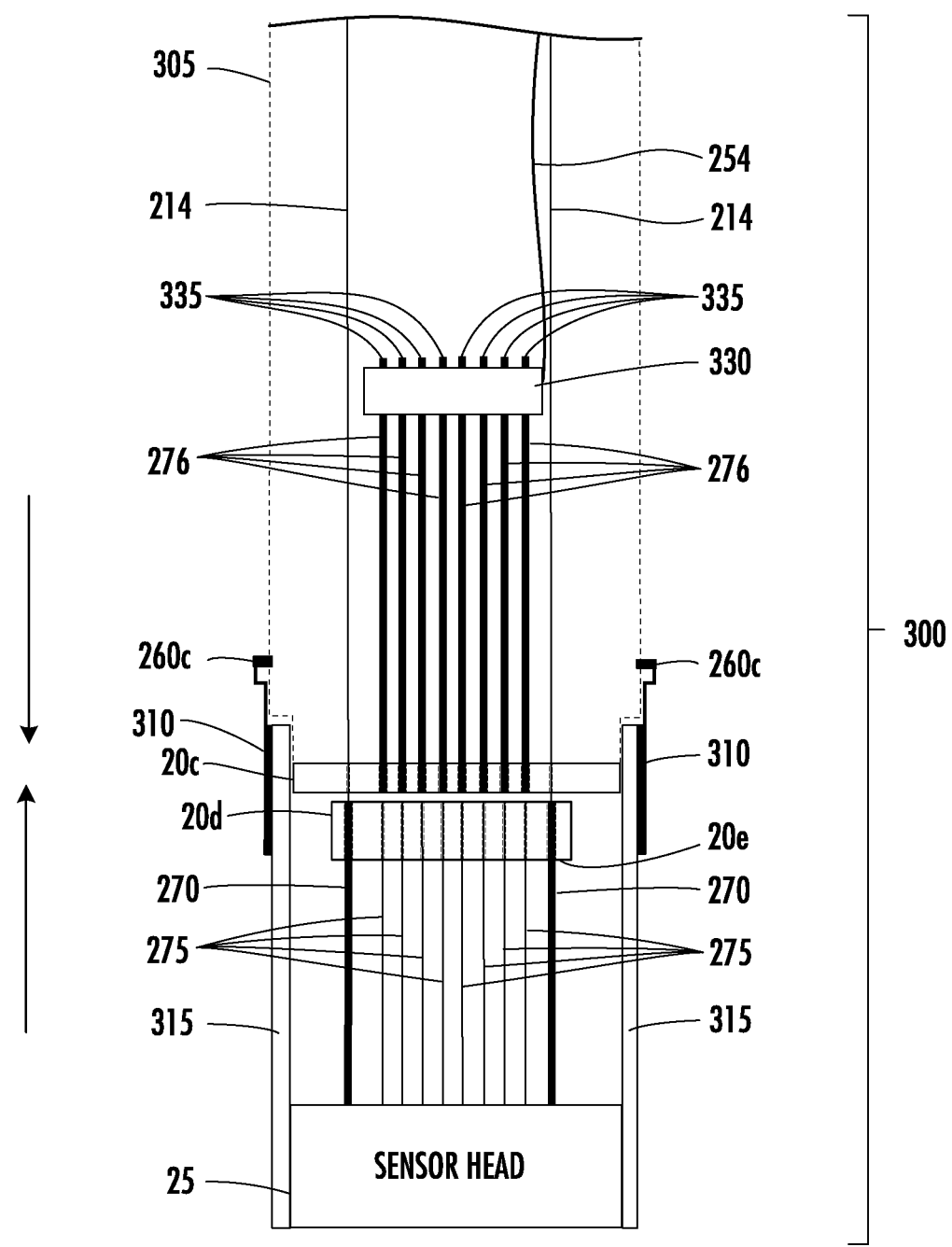

FIGS. 3A-3D show a portion 300 of the upper laparoscopic tube 210 and the lower laparoscopic tube 15. Portion 300 is also identified in FIGS. 2A-2D. FIG. 3A shows the upper and lower laparoscopic tubes connected together. FIGS. 3B-3D show the upper laparoscopic tube and the lower laparoscopic tube disconnected and separated. FIGS. 3A-3D also show the upper and lower laparoscopic tubes without housings 212 and 217. The upper laparoscopic tube includes an inner housing 305 shown with a dashed line. The upper laparoscopic tube can be generally tubular shaped with an interior space in which various elements of the upper laparoscopic tube are located. Inner housing 305 can be housed inside housing 212 and can extend from a distal end of housing 212 where the distal end is distal with respect to a proximal end of housing 212 that is nearest to housing 219. Inner housing 305 can be metal, such as stainless steel, aluminum, titanium, or a plastic-type material.

Inner housing 305 includes a first portion 305a and a second portion 305b, in an implementation. The first portion is longer than the second portion and is about 2-20 times longer than the second portion. Inner housing 305 can be metal or a plastic-type material.

The lower laparoscopic tube 15 includes a first inner housing 310 and a second inner housing 315. Both the first and second inner housings are generally tubular shaped and have interior spaces in which elements of the lower laparoscopic tube are located. The first and second inner housings 310 and 315 are connected at an inner wall of the first inner housing 310 and an exterior wall of the second inner housing

315. Inner housing 310 and sensor head 25 are at opposite ends (i.e., proximal and distal ends) of the second inner housing 315.

Inner housing 315 includes a first portion 315a and a second portion 315b, in an implementation. Second portion 315b is longer than first portion 315a and is about 2-20 times longer than the first portion. Inner housing 315 can be metal or a plastic-type material.

An inner wall 260b of the end portion 315a of the second inner housing 315 has a first shape and an outer wall 260a of the end portion 305b of the inner housing 305 has a second shape. The first and second shapes are complimentary shapes, which allows for the end portion 305b of inner housing 305 to be slid into and connect the end portion 315a of second inner housing 315. Specifically, when the end portion 305b of the inner housing 305 is inserted into the end portion 315a of the inner housing 315, as shown in FIG. 3A, the outer wall 260a of the second portion 305b contacts the inner wall 260b of the second inner housing 315 of laparoscopic tube 15. The contacted inner and outer walls guide the two laparoscopic tubes together.

In an implementation where the outer wall 260b of the end portion 315a is circular and the inner wall 260a of the end portion 305b is circular, an inner diameter of the inner wall is greater than the outer diameter of the outer wall. The outer diameter of the end portion 305b of the inner housing 305a can be about 0.02-0.10 millimeters less than the inner diameter of the end portion 315a inner housing 315. In an implementation, the outer wall 260a and the inner wall 260b are keyed, such as with a slot and a key so that the end portion 305b of inner housing 315 can slide into the end portion 315a of inner housing 315 in one orientation.

Further, when end portion 305b of inner housing 305 slides into end portion 315a of inner housing 315, the waveguides (e.g., optical fibers) of the upper laparoscopic tube and the waveguides (e.g., optical fibers) of the lower laparoscopic tube align and optically couple due at least in part to the complementary shapes of the outer and inner walls, the described diameters, the keying structures, or any combination of these features.

In an alternative implementation, end portion 315a of inner housing 315 can be slid into and connect to the end portion 305b of inner housing 305. Specifically, end portion 315a of inner housing 315 can slide into end portion 305b of inner housing 305 to align and couple the waveguides of the upper laparoscopic tube to the waveguides of the lower laparoscopic tube. In this implementation, an outer wall of the end portion 315a is circular and an inner wall of the end portion 305b is circular, and an inner diameter of end portion 305b is greater than the outer diameter of end portion 315a. The outer diameter of the end portion 315a of the inner housing 315 can be about 0.02-0.10 millimeters less than the inner diameter of end portion 305b of housing 305. In an implementation, the inner wall of the end portions 305b and the outer wall of end portion 315a are keyed, such as with a slot and a key, so that the end portion 315a of housing 315 can slide into end portion 305b of housing 305 in one orientation.

Alternatively, in an implementation where the upper and lower laparoscopic tubes are not separable, the end portions of inner housings 305 and 315 can be integrally formed, adhered together, such as by an adhesive, a mechanical fastener, another mechanical coupling, other connection types, or one or more of these connectors in any combination.

Inner housing 305 of the upper laparoscopic tube and inner housing 310 of the lower laparoscopic tube include coupling devices that couple the two inner housings. Inner housing 305 includes pins or tabs 260c that can be positioned in respective openings (e.g., apertures or recesses) formed in inner housing 310 of the lower laparoscopic tube, in an implementation. The upper laparoscopic tube includes 1-10 pins or tabs and the lower laparoscopic tube includes 1-10 openings adapted to respectively receive the pins or tabs. In an alternative implementation, inner housing 310 of the lower laparoscopic tube includes pins or tabs 260c that are positioned in respective openings (e.g., apertures or recesses) formed in inner housing 305 of the upper laparoscopic tube, in an implementation. The lower laparoscopic tube includes 1-10 pins or tabs and the upper laparoscopic tube includes 1-10 openings adapted to respectively receive the pins or tabs in the latter described alternative implementation. The pins or tabs can be retractable and spring-loaded to push the pins or tabs back when pressed down.

When the upper laparoscopic tube and the lower laparoscopic tube are in a separated configuration, as shown in FIGS. 3B-3D, and are to be connected by pushing the upper and lower laparoscopic tubes together, the pins or tabs can be pushed into the openings when the upper and lower laparoscopic tubes are pushed together and connected as shown in FIG. 3A. The lower laparoscopic tube can be decoupled from the upper laparoscopic tube by pressing the pins to retract the pins or tabs from the apertures.

In an implementation, optical coupler 20c forms the bottom wall of inner housing 305. Optical coupler 20c includes a number of apertures 337 and 339, which extend from a first side 20c1 (e.g., a bottom surface) of the optical coupler to a second side 20c2 (e.g., a top surface) of the optical coupler. The apertures are shown in dashed lines in FIGS. 3A-3D. The number of apertures 337 matches the number of waveguides 276 and matches the number of waveguides 275. The number of apertures 237 can be from 1-20. The number of apertures 339 matches the number of waveguides 214 and matches the number of waveguides 270. The number of apertures 239 can be from 1-10. The number of apertures formed in the optical coupler corresponds to the number of waveguides housed by the upper laparoscopic tube 210 and can be from 3-30 waveguides (e.g., 10 waveguides). The ends of detector waveguides 276 are located in apertures 337 and the ends of source waveguides 214 are located in apertures 339.

The bottom surface 20c1 of optical coupler 20c is a relatively flat surface that can be polished flat. The ends of waveguides 276 and 214 are flush with bottom surface 20c1. The ends of the waveguides are also polished, in an implementation. The ends of the waveguides can also be coated with an antireflection coating.

Optical coupler 20d includes a number of apertures 336 and 338 that extend from a first side 20d1 (e.g., top surface) of the optical coupler to a second side 20d2 (bottom surface) of the coupler, in an implementation. The apertures are shown in dashed lines in FIGS. 3A-3D. The number of apertures 336 matches the number of waveguides 275 and matches the number of waveguides 276. The number of apertures 238 can be from 1-10. The number of apertures 338 matches the number of waveguides 270 and matches the number of waveguides 214. The number of apertures 236 can be from 1-10. The number of apertures formed in the optical coupler corresponds to the number of waveguides housed by the lower laparoscopic tube 150 and can be from 3-30 waveguides (e.g., 10 waveguides). The ends of detector waveguides 275 are located in apertures 336 and the ends of source waveguides 270 are located in apertures 338.

The diameters of the apertures 338 for waveguides 270 are larger than the diameters for the apertures 336 for waveguides 275. The apertures for waveguides 275 can have approximately equal diameters. The apertures for waveguides 270 can also have approximately equal diameters.

The top surface 20d1 of optical coupler 20d is a relatively flat surface that can be polished flat. The ends of waveguides 275 and 270 are flush with top surface 20d1. The ends of the waveguides are also polished, in an implementation. The ends of the waveguides can also be coated with an antireflection coating.

In an implementation, the diameters of the apertures 337 for waveguides 276 are larger than the diameters for the apertures 336 for waveguides 275. The diameters of the apertures 338 for waveguides 270 are larger than the diameters for the apertures 339 for waveguides 214. In other implementations, the diameters of apertures 337 and 336 have other diameters, such as the diameters of apertures 337 being equal to or smaller than the diameters of apertures 336. In other implementations, the diameters of the apertures 338 are equal to or smaller than the diameters for the apertures 339 for waveguides 214. In an implementation, the apertures 337 for waveguides 276 can have approximately equal diameters. The apertures 339 for waveguides 214 can also have approximately equal diameters. The apertures 336 for waveguides 275 can have approximately equal diameters. The apertures 338 for waveguides 270 can also have approximately equal diameters.

When the upper laparoscopic tube and the lower laparoscopic tube are moved toward each other in the direction indicated by the upward and downward arrows on the left side of FIG. 3C, the lower portion 305b of inner housing 305 enters the interior space of inner housing 315 of the lower laparoscopic tube. The outer sidewall of lower portion 305b has a complementary shape with the inner sidewall of inner housing 315. The outer sidewall of the lower portion 305b also contacts the interior sidewall of inner housing 315 when the upper and lower laparoscopic tubes contact. Because the outer and inner sidewalls have complimentary shapes and contact, the tips of waveguides 276 respectively align with the top openings of apertures 336 and the tips of waveguides 214 respectively align with the top openings of apertures 338.

As the lower portion 305b moves further into the interior space of inner housing 315, the surfaces 20c1 and 20d1 may contact, the tips of waveguides 214 respectively contact the tips of waveguides 270, and the tips of waveguides 276 contact the tips of waveguides 275. When pins or tabs 260c are inserted and locked into the openings in housing 310, a spring force is applied by the pin or tabs being located in the openings in housing 310 to hold the tips of waveguides 214 respectively in contact with the tips of waveguides 270, hold the tips of waveguides 276 in contact with the tips of waveguides 275, and may hold surfaces 20c1 and 20d1 in contact. Other devices can be used to apply the spring force.

In an implementation, upper laparoscopic tube 210 includes an aperture plate 330. The aperture plate can be located in inner housing 305. Aperture plate 330 can be a printed circuit board (PCB). The aperture plate has a number of apertures formed in the plate where the apertures extend from a first side of the aperture plate to a second side of the aperture plate. The number of apertures may be the same number as the number of waveguides 276, such as 1-20 waveguides (e.g., 8 waveguides). End portions of waveguides 276 are positioned in the apertures of the aperture plate entering the aperture plate from the first side of the plate. The aperture plate includes photodetectors 335 that are located at openings of the apertures on the second side of the plate. The detectors can be photodetectors, such as photodiodes (e.g., a PN photodiode, a PIN photodiode, an avalanche photodiode, a Schottky photodiode, or other types of photodiodes), photoresistors, phototransistors, metal-semiconductor-metal semiconductor devices, photoconductive detectors, phototubes, such as photoemissive detectors, phototubes, such as photomultipliers, carbon nanotubes (CNTs), or other types of photodetectors.

In an implementation, photodetectors 335 are located just above the apertures formed in aperture plate 330. In an alternative implementation, the photodetectors are connected to the aperture plate, such as via solder, an adhesive (e.g., epoxy resin), or mechanically (e.g., a fastener, bracket, or another device), or any combination of these devices in any combination. The end portions of waveguides 276 either contact the photodetectors or an air gap exists between the ends and the photodetectors so that light received by waveguides 276 is transmitted to the photodetectors from the ends of the waveguides. A number of electrical conductors 254 (e.g., a ribbon cable) are connected to the aperture plate to provide ground, deliver battery power to the photodetectors, and to collect and transmit a number of detector signals generated by the photodetectors and transmit the signals to the TIAs 256.

In an implementation, plate 330 includes a set of apertures that the source waveguides extend through and does not include apertures in which the ends of the detector waveguides are located. That is, the ends of the detector waveguides are not in an aperture plate. Further, the photodetectors are located on the side of plate 330 that faces the sensor head and from which the detector waveguides extend from the sensor head. The detector waveguides are optically coupled to the detector waveguides on the side of place 330 that faces towards the sensor head from which the detector waveguides extend from the sensor head.

When the photodetectors convert received light into electrical signals, the TIAs 256 amplify the electrical signal. Each photodetector may be electrically connected to one TIA by electrical conductors 254. In an implementation, multiple photodetectors are connected to a single TIA, for example, via a multiplexer. The TIAs are adapted to receive analog detector responses generated by the photodetectors. The TIAs convert the current for the analog detector responses to a voltage and amplify the voltage. The fixed gain amplifier 257 and the processor-controlled amplifier respectively amplify the voltage signals to levels that the ADCs can convert to digital signals that are used by the processor.

In the implementation shown in FIG. 2A, for example, the TIAs may amplify low current signals generated by one or more photodetectors 335 to stable voltage signals, the fixed gain amplifier may amplify the stable voltages output from the TIAs to higher voltages, and the processor-controlled amplifier may amplify the higher voltages output by the fixed gain amplifier to voltages usable by the ADC.

In the implementation shown in FIG. 2B, for example, the TIAs may amplify low current signals generated by one or more photodetectors 335 to stable voltage signals, the processor-controlled amplifier may amplify the voltages output from the TIAs to higher voltages, and the fixed gain amplifier may amplify the higher voltages output by the processor-controlled amplifier to voltages that are usable by the ADC.

The ADCs sample the analog signals at a sampling rate. For example, the sampling rate can be about on the order of kilohertz, such as about 200-300 kilohertz. The measurement rate that the processor operates on the digitized signals is less than the sampling rate. The measurement rate that the processor operates on the digitized signals is about 1-3 hertz (depending on the conditions of the oximeter probe). In other implementations, the measurement rate can be above 3 hertz, such as from about 4 hertz to about 1 kilohertz. Generally, the faster the sampling rate of the ADCs and the operating frequency of the processor, the more power that is consumed, which is a consideration for a battery-operated device, and also the data generated increases with the sample rate.

When using a measurement rate of about 0.33 to about 3 hertz, the amount of data can be transmitted wirelessly by the transceiver to other devices (e.g., a computer or a display) using technologies such as Bluetooth and Wi-Fi (and others mentioned in this patent) without data loss. In other implementations, a proprietary wireless technology can be used, such as when higher sampling rates are desired.

The processor can apply one or more calibration calculations to digitized detector responses received from the ADCs, such as performing one or more calibration steps on the data. Calibration can include calibrating the digitized detector responses for inherent discrepancies in the intensity of light emitted by the LED of the light engine, for inherent discrepancies in the detection sensitivity of the photodetectors, or both, or other correlation calculations. Calibration information for the LEDs and photodetectors can be predetermined and stored in communication tag 7.

The processor is adapted to use spatially resolved spectroscopy techniques for determining oximeter information, such as blood oxygen saturation, of tissue from the detector signals that are digitized by the ADCs. Spatially resolved spectroscopy is facilitated by the distances between the source structure and the detector structure of the sensor head. The oximeter information generated by spatially resolved spectroscopy techniques, using near infrared spectroscopy (NIRS) laparoscopically or using NIRS laparoscopically including visible wavelengths, can include perfusion information for tissue that is being probed by the laparoscopic tube, such as an interior organ of a body.

The following U.S. patent applications are incorporated by reference along with all other references cited in this application: Ser. Nos. 13/887,130, 13/887,220, 13/887,213, 13/887,178, and 13/887,152, filed May 3, 2013; Ser. No. 13/965,156, filed Aug. 26, 2013; Ser. Nos. 15/493,132, 15/493,111, 15/493,121, filed Apr. 20, 2017; Ser. No. 15/494,444, filed Apr. 21, 2017; and Ser. Nos. 15/495,194, 15/495,205, and 15/495,212, filed Apr. 24, 2017. The above applications describe various laparoscopic oximeters and oximetry operations, such as spatially resolved spectroscopy, and discussion in the above applications can be combined with aspects of the invention described in this application, in any combination.

In an implementation, the outer housing 212 and 217 can be the same or different materials. For example, the outer housing of the lower laparoscopic tube 15 can be stainless steel and the outer housing of the upper laparoscopic tube 210 can be a plastic material. One or both of the lower and upper laparoscopic tubes can also be coated, such as with a polymeric coating to make the surface nonconducting. The outer housings 212 and 217 can be a single tube into which housings 210 and 15 are inserted. In an implementation, outer housings 212 and 217 are a trocar into which housings 305 and 310 are inserted for use.

Figure 4A:
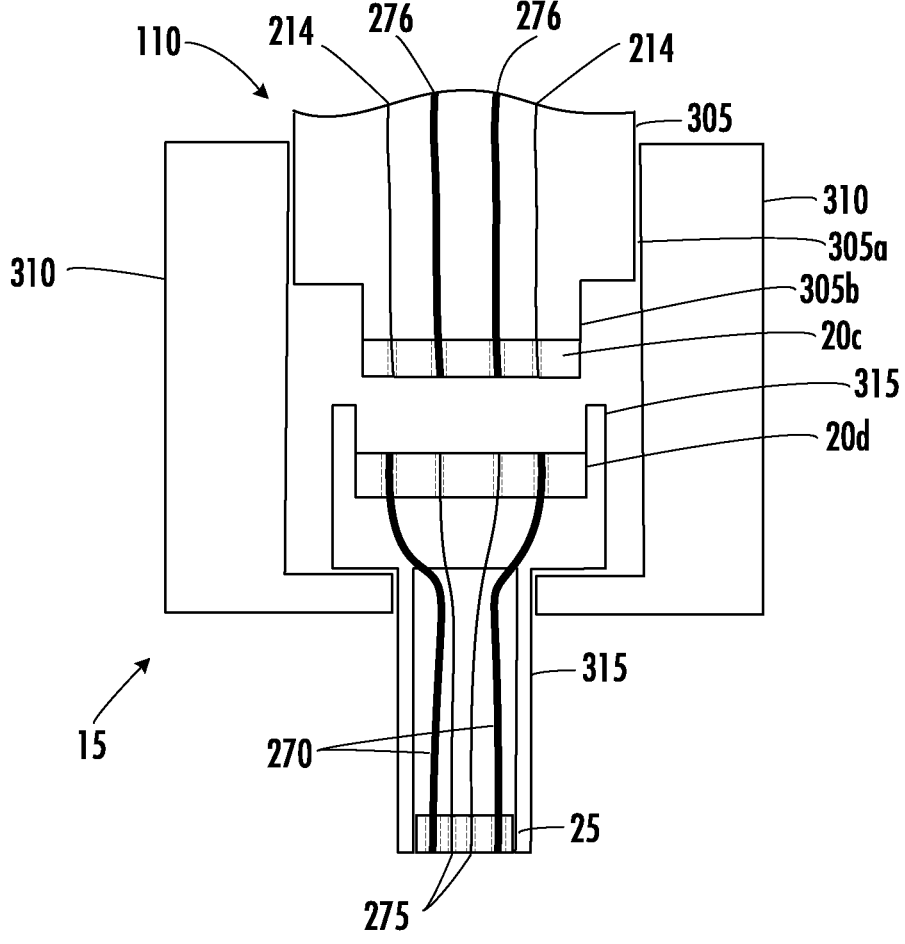
FIGS. 4A-4B show the upper laparoscopic tube and the lower laparoscopic tube, in an implementation.
Figure 4B:
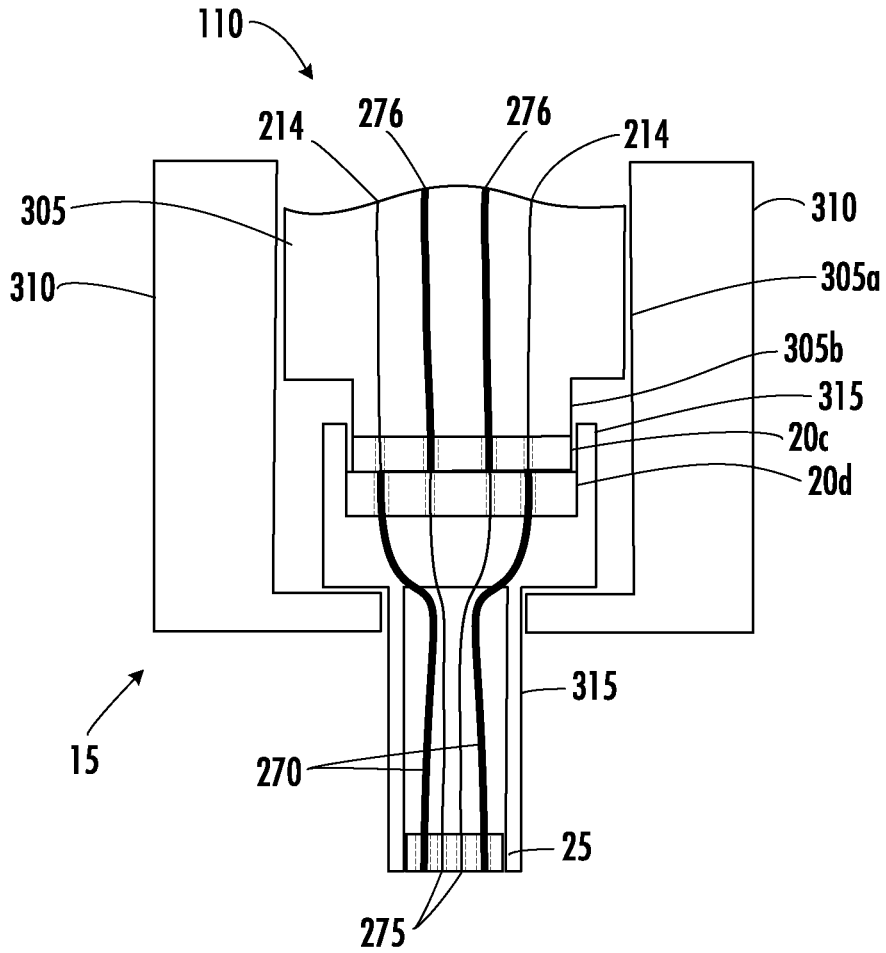

FIGS. 4A-4B show the upper laparoscopic tube 110 and the lower laparoscopic tube 15, in an implementation. In FIG. 4A, inner housing 305 is partially positioned in a first opening (e.g., a proximal opening) at the top of inner housing 310, but the lower portion 305b of inner housing 305 is not in contact with optical coupler 20c. Further, the waveguides are not coupled.

In FIG. 4B, the lower portion 305b of inner housing 305 is in a first opening (e.g., a proximal opening) at the top of inner housing 315 and the lower portion 305b is in contact with optical coupler 20 inside this first opening. Waveguides 214 and 270 are butted together and the waveguides 275 and 276 are butted together in the first opening in inner housing 315. Housings 305 and 310 can be coupled together via coupling mechanisms described above, such as pins interested into apertures, screw devices, or other devices.

In the implementation, optical coupler 20c is located in the first opening that is at the top of inner housing 315. The optical couplers 20d and 20c connect within the proximal opening at the end of inner housing 315.

The apertures in the optical couplers 20c-20d that house the ends of the waveguides are shown with dashed lines. Waveguides 214 and 270 are butted together in the first opening at the end of inner housing 315 and the waveguides 275 and 276 are butted together in this first opening of inner housing 315. The sensor head 25 is located in a second opening (e.g., a distal opening) at the second end of inner housing 315. The apertures in the sensor head that house the ends of the waveguides are shown with dashed lines.

Figure 5:
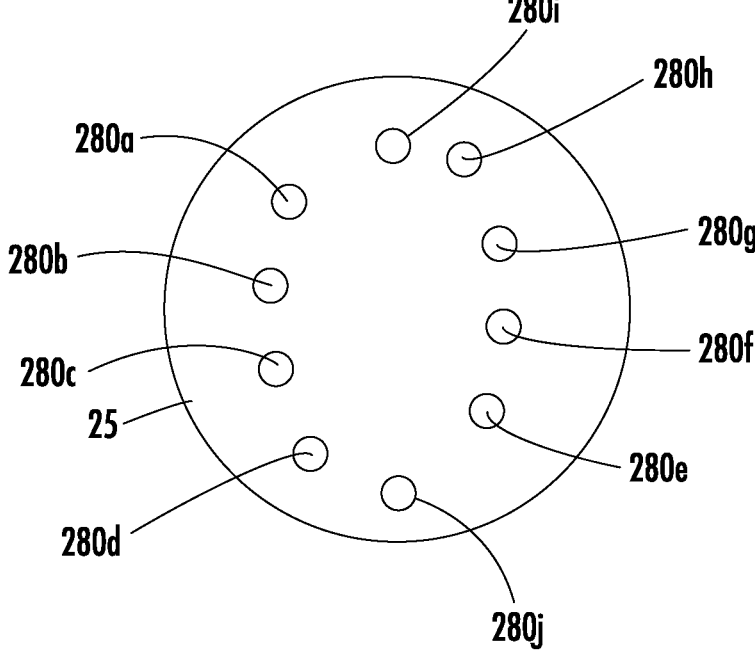
FIG. 5 shows an end view of the sensor head, in an implementation.

FIG. 5 shows an end view of the sensor head 25, in an implementation. The sensor head includes source structures 280i-280j and includes detector structures 280a-280h, in an implementation. The sensor head can include more or fewer source structures and more or fewer detector structures. The source structures emit light from waveguides 270 of the lower laparoscopic tube and the detector structures detect light reflected from tissue, such as patient tissue or a tissue proxy. The detector structures can transmit light to waveguides 275 of the lower laparoscopic tube. The source structures and detector structures can include the portions of the waveguides (e.g., portions of the waveguides located in the apertures, the tips of the terminal ends of waveguides, or both), other waveguides (e.g., epoxy located in the apertures) that optically couple to the waveguides, the apertures, other structures, or any combination of these structures.

Spatially resolved spectroscopy is facilitated by the source structure to detector structures distances of the sensor head where at least one source structure to detector structure distance is less than 1.5 millimeters and can be less than one millimeter, and at least one source structure to detector structure distance is greater than 2.5 millimeters or at least two source structure to detector structure distances are greater than 2.5 millimeters. The source structure to detector structure distances can be achieved via a number of source and detector combinations, such as one source and two detectors, two sources and one detector, or other combinations.

Spatially resolved spectroscopy is further facilitated by the memory storing and the processor using a number of simulated reflectance curves, where each of the reflectance curves represents an absorption coefficient and a scattering coefficient for the particular configuration of source structures and detector structures of the sensor head.

The simulated reflectance curves include reflectance intensities (e.g., in arbitrary units) for light reflected from simulated tissue for a variety of wavelengths emitted from the oximeter probe. The simulated reflectance curves can be of simulated tissue using a Monte Carlo simulation method, a diffusion approximation method, or other simulations.

The processor can determine one or more of the simulated reflectance curves that best fits (e.g., lowest fit error determined by a fit method, such as least squared or others) reflectance data generated by the detectors. The processor can then determine one or more absorption coefficients and one or more scattering coefficients for the tissue from the one or more simulated reflectance curves that best fits the reflectance data. From the absorption coefficient, the processor can then determine other oximeter information for measured tissue, such as oxygen saturation. The source structure to detector structure distances of the sensor head facilitates that the absorption coefficient and the reduced scattering coefficient can be determined from the simulated reflectance curves where these coefficients are mathematically independent. Because the absorption coefficient and the reduced scattering coefficient are mathematically independent, further tissue measurements, further mathematical determinations, or both can be avoided, via the use of such spatially resolved spectroscopy.

This detailed description describes examples of implementations with specific measurements, angles, values, dimensions, shapes, and orientations. These examples implementations are not intended to be exhaustive or to limit the invention to the precise form described.

The measurements, for example, in millimeters or centimeters are approximate values. The values can vary due to, for example, measurement or manufacturing tolerances (as will be understood by those of ordinary skill in the art) or other factors (as will be further understood by those of ordinary skill in the art). A measurement can vary, for example, by plus or minus 1 percent, plus or minus 5 percent, plus or minus 10 percent, plus or minus 15 percent, plus or minus 20 percent, plus or minus 1 to 5 percent, plus or minus 5 to 10 percent, or plus or minus 15 to 20 percent. Further, the measurements are for a specific implementation of the device, and other implementations can have different values, such as certain measurements, dimensions, or both made longer to accommodate smaller hands or larger hands or to access tissue in a particular location of a patient's body.

For the specific implementations described, some specific values, ranges of values, and numbers are provided. These values indicate, for example, dimension, angles, ranges, frequencies, wavelengths, numbers, a relationship (e.g., relative value), and other quantities (e.g., numbers of sensors, sources, detectors, diodes, fiber optic cables, and so forth). Some measurements are for a specific implementation of the device, and other implementations can have different values, such as certain dimensions made larger for a larger-sized product, or smaller for a smaller-sized product. The device may be made proportionally larger or smaller by adjusting relative measurements proportionally (e.g., maintaining the same or about the same ratio between different measurements). In various implementations, the values (or numbers or quantities) can be the same as the value given, about the same of the value given, at least or greater than the value given, or can be at most or less than the value given, or any combination of these. The values (or numbers or quantities) can also be within a range of any two values given or a range including the two values given. When a range is given, the range can also include any number within that range to any other number within that range.

The dimensions, for example, along an axis, a rotational orientation, or both are approximate values. The dimensions can be in values, directions, angles, or any combination of these dimension. Dimensions, for example, of values in millimeters or centimeters, of directions along an axis or at an angular orientation relative to an axis, of an angular orientation are approximate values. The values, direction, and angles can vary due to, for example, measurement or manufacturing tolerances or other factors. A dimension can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, plus or minus 20 percent, plus or minus 0.1 to 0.2 percent, plus or minus 0.2 to 0.5 percent, plus or minus 0.5 to 1 percent, plus or minus 1 to 5 percent, plus or minus 5 to 10 percent, plus or minus 10 to 15 percent, or plus or minus 15 to 20 percent.

The shapes, for example, a geometric shape can be approximate shapes. The shapes can be in values, directions, angles, terms, or any combination of these shapes. The shapes can vary due to, for example, measurement or manufacturing tolerances or other factors. A shape can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, plus or minus 20 percent, plus or minus 0.1 to 0.2 percent, plus or minus 0.2 to 0.5 percent, plus or minus 0.5 to 1 percent, plus or minus 1 to 5 percent, plus or minus 5 to 10 percent, plus or minus 10 to 15 percent, or plus or minus 15 to 20 percent.

The orientations, for example, parallel, perpendicular, transverse, and angle are approximate values. The orientation can be in values, directions, angles, terms, or any combination of these orientations. Orientations, for example, of terms or angles can be approximate orientations. The orientations vary due to, for example, measurement or manufacturing tolerances or other factors. An orientation can vary, for example, by plus or minus 0.1 percent, plus or minus 0.2 percent, plus or minus 0.5 percent, plus or minus 1 percent, plus or minus 5 percent, plus or minus 10 percent, plus or minus 15 percent, or plus or minus 20 percent. Terms, such as about, substantially, approximately, or other relative terms can include the described ranges as will be readily understood by those of ordinary skill in the art and can include ranges that will be understood by those of ordinary skill in the art.

Figure 6A:
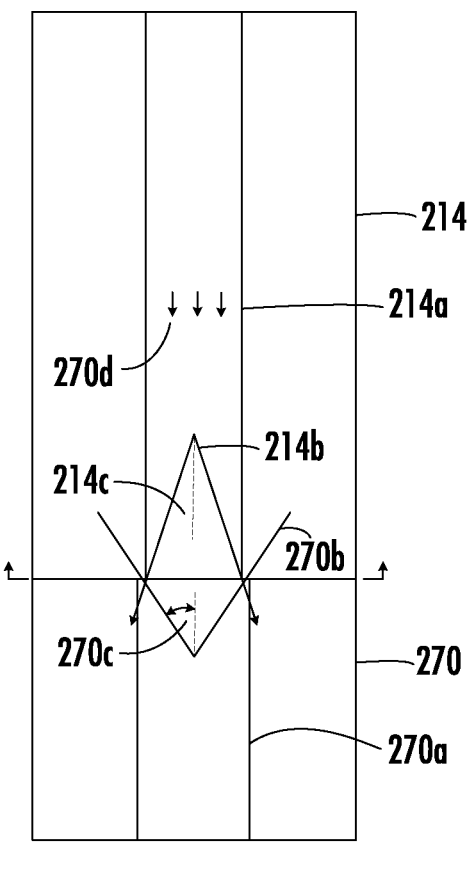
FIGS. 6A and 7A, respectively, show the transmit waveguides (e.g., transmit optical fibers) butt connected to the receive waveguides (e.g., receive optical fibers).
Figure 7A:
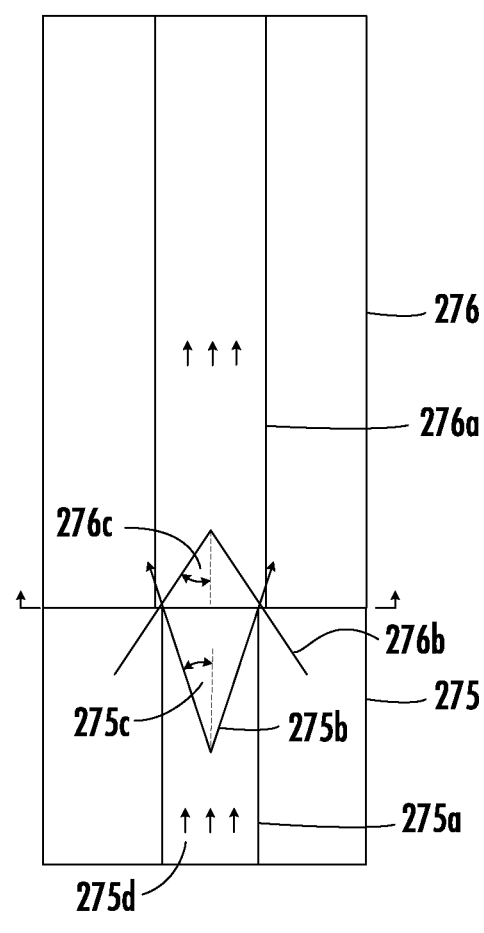

FIGS. 6A and 7A respectively show one of the waveguides 214 butt connected to one of the waveguides 270 and show one of the waveguides 275 butt connected to one of the waveguides 276. When the tips of the core 214a of waveguide 214 and the core 270a of waveguide 270 are in contact, light can be transmitted from waveguide 214 into waveguide 270. The downward arrows 270d in FIG. 6A show the direction of the travel of light from one of the waveguides 214 to one of the waveguides 270. More specifically, light generated and emitted from the light engine can be transmitted into waveguides 214, and thereafter, the light can be transmitted from waveguides 214 into waveguides 270. Thereafter the light can be transmitted from waveguides 270 into the sensor head. The light can be transmitted from the source structures of the sensor head. The light can be transmitted from the source structures into tissue or into a tissue proxy, such as a calibration medium that is used when calibrating the oximeter probe. After the light enters tissue (or tissue proxy) and reflected light is reflected back towards the sensor head, the reflected light is collected by detector structures of the sensor head. The reflected light enters waveguides 275 and thereafter is transmitted from waveguides 275 to waveguides 276. The upward arrows 275d in FIG. 7A show the direction of the travel of the reflected light from one of the waveguides 275 to one of the waveguides 276. After the reflected light is transmitted into waveguides 276, these waveguides transmit this reflected light to the photodetectors 335.

The photodetectors generate detector signals based on the reflected light received by the photodetectors from waveguides 276. The detector signals are electrical signals that are transmitted out from the photodetectors through the aperture plate 300 (e.g., through electrical traces of the aperture plate) and conductors 254 to the TIAs 256 located in the probe unit.

In an implementation, the core 214a of each transmit waveguide 214 has a diameter and numerical aperture that is less than the diameter and numerical aperture of the core 270a of each receive waveguide 270. The numerical apertures of waveguides 214 and 275 can be equal, the numerical aperture of waveguides 270 and 276 can be equal, or both. The diameters of waveguides 214 and 275 can be equal, the diameters of waveguides 270 and 276 can be equal, or both.

In an implementation, an optical element is positioned between the ends of optical fibers 214 and 270. The optical element can contact the ends of the optical fibers. The optical element can be a lens, a flat disk with substantially parallel sides that can contact the ends of the optical fibers, an elastic element that deforms to make contact with the ends of the optical fibers, or another element. The lens or flat element can be glass, plastic, or a plastic type material. The index of refraction of the flat element can match the refractive indices of one or both of the cores of the optical fibers.

Each transmit waveguide 214 emits light into an emission cone 214b, which has an emission angle 214c. The emission angle of a waveguide is the maximum transmission angle of light that is transmitted from a waveguide. The emission angle is measured from a normal of the end of the waveguide to the maximum transmission angle.

Each receive waveguide 270 has an acceptance cone 270b, where light received in the acceptance cone can be transmitted into the fiber for transmission in the fiber. Light not received in the acceptance cone is either not transmitted into the waveguide or has a low probability of being transmitted into the waveguide. The acceptance cone has an acceptance angle 270c. The acceptance angle is measured from a normal at the end of the waveguide to the maximum incidence angle at which light is transmitted into the waveguide. The numerical aperture is the sine of the emission angle or the acceptance angle and is a dimensionless number that characterizes the range of angles over which a waveguide can emit or accept light.

Emission angle 214c is less than acceptance angle 270c, in an implementation. Emission angle 214c is less than acceptance angle 270c by 1-30 degrees. Providing for emission angle 214c to be less than the acceptance angle 270c allows for a relatively high percentage (e.g., up to 96 percent) of light emitted from waveguide 214 to be accepted by waveguide 270. The light that does not enter waveguide 270 may be reflected back from the tip of waveguide 270 towards the tip of waveguide 214.

The core 275a of each transmit waveguide 275 has a diameter and numerical aperture that is less than the diameter and numerical aperture of each core 276a of each receive waveguide 276, in an implementation. Each transmit waveguide 275 emits light into an emission cone 275b, which has an emission angle 275c. Each receive waveguide 276 has an acceptance cone 276b, where the acceptance cone has an acceptance angle 276c. Light received in the acceptance cone can be transmitted into the fiber for transmission in the fiber. Light not received in the acceptance cone is either not transmitted into the waveguide or has a low probability of being transmitted into the waveguide.

Emission angle 275c is less than acceptance angle 276c, in an implementation. Emission angle 275c is less than acceptance angle 276c by 1-30 degrees. Providing for emission angle 275c to be less than the acceptance angle 276c allows for a relatively high percentage (e.g., up to 96) of light emitted from waveguide 275 to be accepted by waveguide 276. The light that does not enter waveguide 276 may be reflected back from the top surface of waveguide 276 towards the tip of waveguide 275. Multiple reflections may be a relatively constant noise signal.

The differences between the diameters and the numerical apertures of the cores of the transmit waveguides 214 and the receive waveguides 270 and the between the cores of the transmit waveguides 275 and receive waveguides 276 allow for the waveguides to be connected but misaligned while the percentage of light transmitted from the transmit waveguides and receive waveguides is the same for the configuration where the centers of the cores of the transmit and receive waveguides are aligned.

Figure 6B:
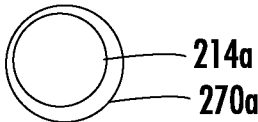
FIG. 6B shows the cross-section of the cores of the transmit and receive waveguides (e.g., receive optical fibers) where the cores butt together.

FIG. 6B shows the cross-section of the cores of waveguides 214 and 270 where the cores butt together. FIG. 6B also shows that the cores of the waveguides are misaligned, but the perimeter of the end of core 214a is within the perimeter of the end of core 270a.

Figure 7B:
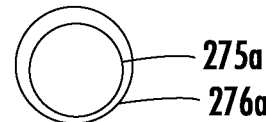
FIG. 7B shows the cross-section of the cores of the transmit and receive waveguides (e.g., receive optical fibers) where the cores butt together.

FIG. 7B shows the cross-section of the cores of waveguides 275 and 276 where the cores butt together. FIG. 7B also shows that the cores of the waveguides are misaligned, but the perimeter of the end of core 275a is within the perimeter of the end of core 276a.

With the center lines of cores 214a and 270a misaligned but with the perimeter of the end of core 214a within the perimeter of the end of core 270a, the percentage of light transmitted from the transmit core to the receive core is the same as if the centers of the core aligned. The percentage of light transmitted from a transmit waveguide to a receive waveguide is the same if the centers of the cores of these waveguides are aligned or misaligned as shown in FIG. 6B because the diameter and numerical aperture of the core of the transmit waveguide are less than the diameter and numerical aperture of the core of the receive optical.

Similarly, with the center lines of cores 275a and 276a misaligned but with the perimeter of the end of core 275a within the perimeter of the end of core 276a, the percentage of light transmitted from the transmit core to the receive core is the same as if the centers of the cores are aligned. The percentage of light transmitted from a transmit waveguide to a receive waveguide is the same as if the centers of the cores of these waveguides are aligned or misaligned as shown in FIG. 7B, because the diameter and numerical aperture of the core of the transmit waveguide are less than the diameter and numerical aperture of the core of the receive optical. Allowing for the misalignment of the cores of the transmit and receive waveguides as shown in FIGS. 6B and 7B further allows for the end 305b of inner housing to misalign with the opening of inner housing 315 when the end 305b is positioned inside the opening of inner housing 315 while maintaining a percentage of light transmission for when the end 305b and the opening of housing 315 are aligned and for when the cores of the transmit and receive waveguides are aligned. That is, an amount of tolerance (or slop) is permitted when the laparoscopic tube is connected to the probe unit to form the oximeter probe and the oximeter probe can make reliable oximetry measurements.

In an implementation, the laparoscopic tube is calibrated and the calibration information for the laparoscopic tube is stored in NFC tag 7. Calibration information for the laparoscopic tube can be generated by measuring a percentage of the transmission of light for a known amount of light transmitted into each waveguide 270, by measuring a percentage of the transmission of light for a known amount of light transmitted into each waveguide 275, or both. Other calibration methods for the laparoscopic tube can be used as will be understood by those of ordinary skill in the art.

When the laparoscopic tube is connected to the probe unit to form the oximeter device 5, the NFC tag reader 8 of the probe unit can access and read the calibration information stored in the NFC tag 7. The calibration information collected by the NFC tag reader can be used by the processor to calibrate the laparoscopic tube. More specifically, the calibration information retrieved from the NFC tag 7 can be stored in memory 222 and retrieved and used by the processor before or when oximetry measurements are made. Further, when different laparoscopic tubes are attached to the probe unit, calibration information specific to each laparoscopic unit can be collected by the NFC tag reader and be used by the processor to uniquely calibrate each laparoscopic tube.

Other devices and transmission protocols can be used to transmit calibration information for the laparoscopic tube to the probe unit. For example, calibration information can be supplied to the probe unit via a computer that stores the calibration information. The transmission protocol may be an Ethernet protocol, a USB protocol, a UART protocol (i.e., universal asynchronous receiver transmitter protocol), a USART protocol (i.e., a universal synchronous asynchronous receiver transmitter protocol), an SPI Protocol (i.e., serial peripheral interface bus protocol), or another wired communication protocol.

A wireless communication link can also be used to transmit the calibration information from a computer to the probe unit. The wireless communication link can operate according to one of a variety of protocols, such as one of the Bluetooth protocols (e.g., Bluetooth, Bluetooth SMART, Bluetooth Low Energy, others), one of the IEEE 802.11 protocols, ANT, 6LoWPAN, MyriaNed, EnOcean, Z-Wave, Wi-Fi, one of the IEEE 802.15.4 protocol, such as ZigBee, or others. These or other wireless protocols can be used by the probe unit to receive and transfer data to and from a computer system.

The wireless link between the oximeter probe and the computer system is a direct wireless connection in an implementation. That is, no intermediary transmitter circuits, receiver circuits, or transceiver circuits receive the wireless signal transmitted from the computer system to the probe unit for subsequent retransmission of the wireless signal to the probe unit. Similarly, no intermediary transmitter circuits, receiver circuits, or transceiver circuits receive the wireless signal transmitted from the probe unit to the computer system for subsequent retransmission of the wireless signal to the computer system.

In an implementation, the probe unit includes a user interface via which a user can enter the calibration information for a laparoscopic element. The user interface can be a user interface of the display 224 that can include a touch screen adapted to receive the user input for the calibration information. The probe unit can include other user input devices, such as one or more buttons or a keypad, adapted for receiving the calibration information.

Figure 8:
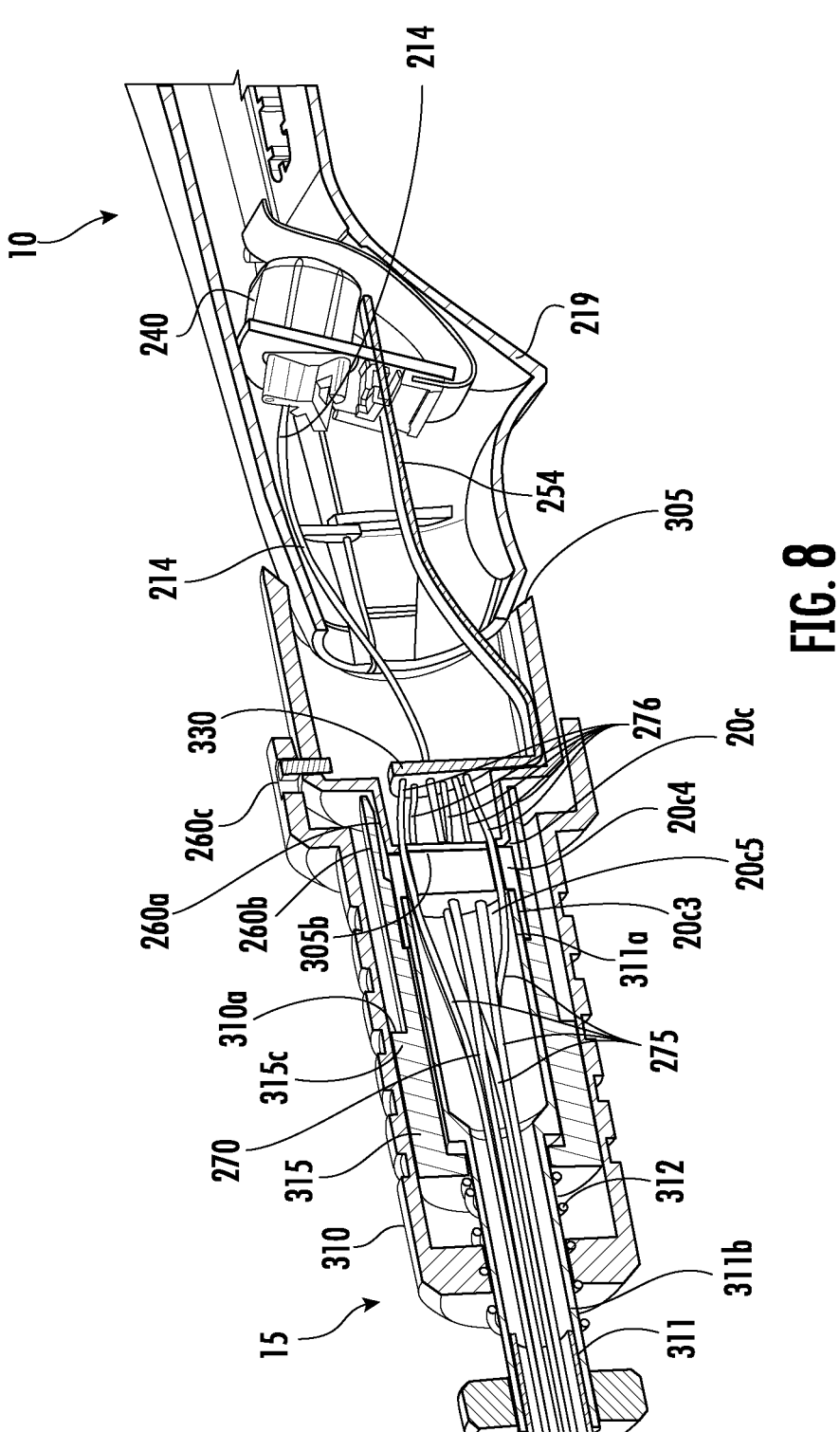
FIG. 8 shows a cross-sectional view of a portion of the probe unit, the upper laparoscopic tube, and the replaceable lower laparoscopic tube, in an implementation.

FIG. 8 shows a cross-sectional view of a portion of the probe unit 10, the upper laparoscopic tube 210, and the replaceable lower laparoscopic tube 15, in an implementation. The cross-sectional view shows the lower laparoscopic tube removably connected to the upper laparoscopic tube. The lower and upper laparoscopic tubes are held together by pin 260c of inner housing 305 positioned in an aperture in the first inner housing 310. The lower and upper laparoscopic tubes can be held together by other or additional devices. The pin can be pressed in to release the pin from the aperture to release the connection between the lower and upper laparoscopic tubes.

In an implementation, the lower laparoscopic tube includes a housing 311 that is in part housed in both of housings 310 and 315 and extends from these housings through apertures formed in the ends of housings 310 and 315. Housing 311 has a first end portion 311a and a second end portion 311b that are both tubular or other shapes having open interior spaces. First end portion 311a is positioned in an interior space 20c3 of optical coupler 20c. The optical coupler includes a waveguide coupling block 20c4 and a tubular extension 20c5 connected to the coupling block that forms interior space 20c3. The second end portion is located outside of the interior spaces of housing 310 and 315. The sensor head of the lower laparoscopic tube can be connected at the end of housing 311.

The lower laparoscopic tube includes a spring 312 located in the interior space of housing 310 and is positioned between the end portions of housing 310 and housing 315. The spring provides a spring force that pushes housing 315 against housing 311 and optical coupler 265. The spring force provides cushioning when housing 305 of the upper laparoscopic tube is inserted into housing 315. More specifically, the spring force provides cushioning when the end portion of housing 305 is pressed against the optical coupler to limit the force that the tips of the waveguides of the lower and upper laparoscopic tube exert against each other, preventing the waveguides from damaging each other when being put into contact.

In an implementation, housing 310 has a step 310a and housing 315 has a step 315c. Spring 312 forces steps 310a and 315c into contact. The spring can force the steps into contact before, during, or after the lower laparoscopic tube is connected to the upper laparoscopic tube. The steps can come out of contact when the lower and upper laparoscopic tubes are connected and housing 305 contacts with housing 315, with optical coupler 20c, or both. The steps limit travel of housing 315 in housing 310 in a first direction towards housing 315 and the upper laparoscopic tube. The steps also create a stop position for the optical coupler within housing 310. The stop position of the optical coupler within housing 310 is shown in FIG. 6. The optical coupler can move out of the stop position and up housing 310 when pressed on by housing 305 to provide the cushioning described above. The interior wall of housing 315 can include a number of additional steps, such as a step that contacts a top edge of the tubular portion 20c3 of the optical coupler to set a recess position of the optical coupler inside the interior space of housing 315, which the optical coupler cannot be located past.

Figure 9A:
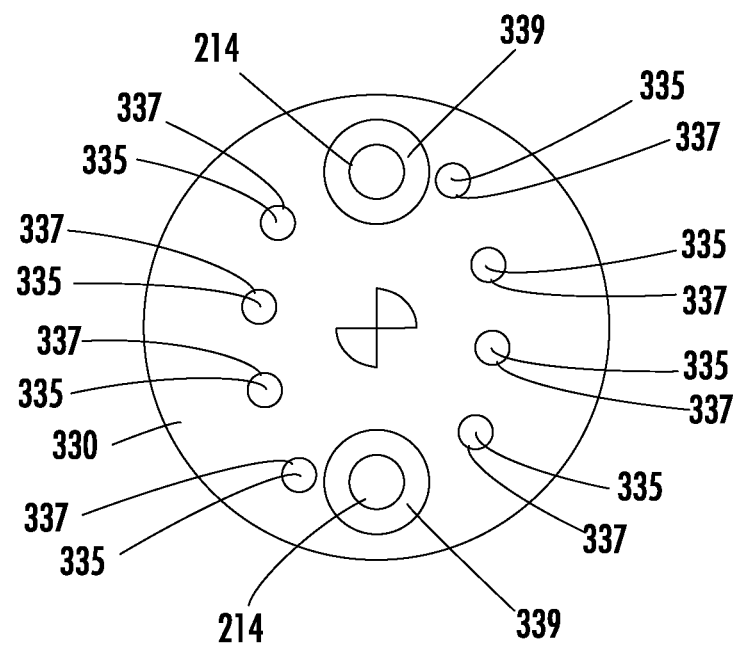
FIGS. 9A-9B show a front view and a back view of the aperture plate.
Figure 9B:
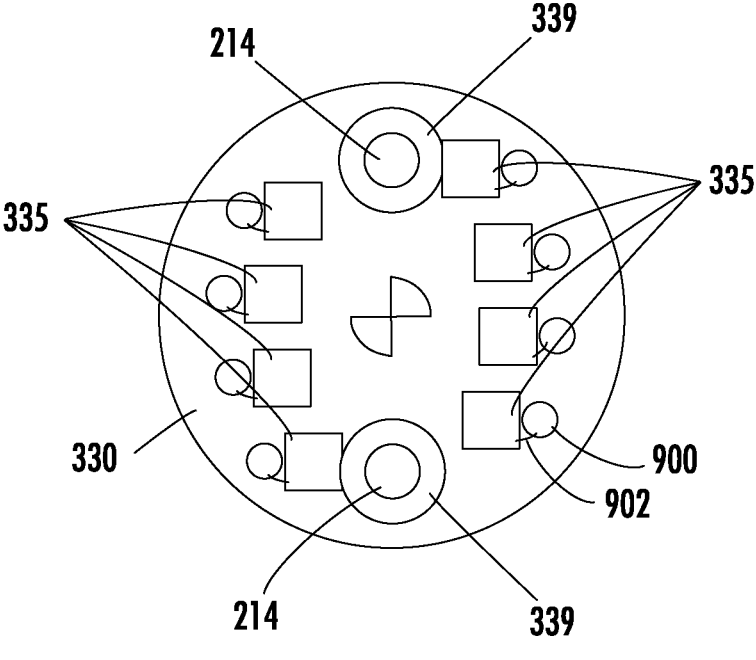

FIGS. 9A-9B show a front view and a back view of aperture plate 330. FIG. 9A shows a number of apertures 337 formed in the aperture plate and a number of apertures 339 formed in the aperture plate. Each of the apertures extends through the aperture plate. The aperture plate includes an aperture 337 (e.g., 1-20) for each photodetector 335 mounted adjacent to (e.g., above) or on the aperture plate and includes an aperture 339 (e.g., 1-10) for each waveguide 214 that extends through the aperture plate. Apertures 337 allow light transmitted from waveguides 276 to pass through the apertures to reach the photodetectors. The light can pass through the aperture while the light is in the waveguides, emitted from waveguides 276, or both.

The aperture plate can be a printed circuit board that includes a number of electrical contacts 900 to which the photodetectors are electrically connected, such as by wires 902. Each photodetector can also be connected to a ground plane, not shown. The aperture plate is connected to cable 254 as shown in FIG. 8 to transmit electrical signals that are generated by the photodetectors to the amplifiers.

Figure 10:
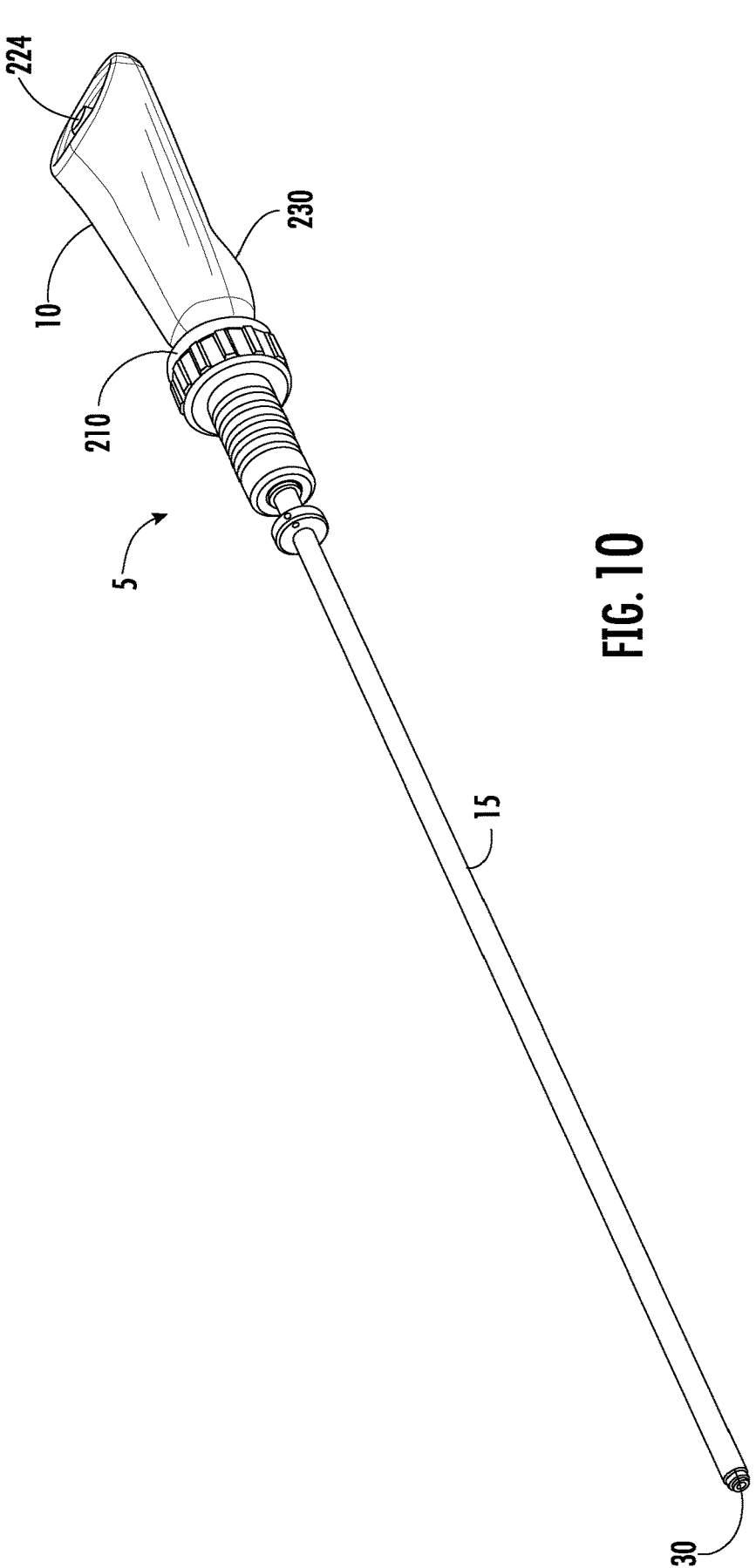
FIG. 10 shows an oximeter probe, in an implementation.

FIG. 10 shows an oximeter probe 5, in an implementation. Oximeter probe 5 includes probe unit 10 connected to replaceable lower laparoscopic tube 15. Probe unit 10 can include upper laparoscopic tube 210 to which the lower laparoscopic tube 15 can connect and disconnect. In one implementation, the battery 230 is contacted in a removable housing that can be removably attached to probe unit 10. The display can be at an opposite end of oximeter probe 5 relative to the replaceable lower laparoscopic tube.

The battery can include one or more of a variety of battery types, such as one or more replaceable batteries, rechargeable batteries, or disposable batteries.

Replaceable batteries are replaceable with charged batteries, such as new batteries, after their stored charge is expended. The replaceable batteries may be batteries that can be purchased over the counter at a store, such as a retail or wholesale store. Rechargeable batteries can be recharged after their stored charge is expended. In an implementation, the rechargeable batteries can be replaceable batteries. Disposable batteries are discarded after their stored charge is expended. Some disposable battery chemistry technologies include non-rechargeable lithium ion, alkaline, zinc carbon, or silver oxide. The battery has sufficient stored charge to allow the use of the handheld device for several hours.

In implementations where the battery is rechargeable, the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via a wireless charging system (e.g., a wireless charging system operating according to the Qi standard or another charging standard), via an AC adapter with a cord that connects to the handheld unit. The circuitry in the display can include a recharger circuit (not shown).

In an implementation, an outer housing of the lower laparoscopic tube embodiments described can be plastic, a plastic-type material, or metal, such as stainless steel or titanium. An outer housing of an upper laparoscopic tube can be plastic, a plastic-type material, or metal, such as stainless steel or titanium. The lower laparoscopic tube has a length of 10 centimeters to 60 centimeters. More specifically, the tip of the sensor head can be one of a variety of distances (e.g., 10 centimeters to 60 centimeters) from the top of the lower laparoscopic tube where the length is based on the particular medical procedure that the oximeter probe is used for.

Optical fibers 270 located in laparoscopic tube 15 can have a variety of lengths, such as from about 10 centimeters to about 60 centimeters. Optical fibers 214 located in probe unit 10 can have a variety of lengths, such as from about 2 centimeters to about 10 centimeters. Each optical fiber 270 is longer than each optical fiber 214. Each optical fibers 270 can be about 5 times to about 30 times longer than each optical fiber 214. Optical fibers 275 located in laparoscopic tube 15 can have a variety of lengths, such as from about 10 centimeters to about 60 centimeters. Optical fibers 276 located in probe unit 10 can have a variety of lengths, such as from about 2 centimeters to about 10 centimeters. Each optical fiber 275 is longer than each optical fiber 276. Each optical fiber 275 can be about 5 times to about 30 times longer than each optical fiber 214.

The upper laparoscopic tube has a length of 1 centimeter to 10 centimeters. The outside cross-sectional dimension of the laparoscopic tube can range from about 3 millimeters to about 20 millimeters or greater (e.g., 3, 4, 5, 6, 7, 8, 9, 10, 15, or 20 millimeters, or others). The cross-sectional shape of the laparoscopic tube can be, for example, a circle, ellipse, oval, or any rounded polygon (e.g., rounded square or rectangle).

The tip of the laparoscopic tube can have a variety of shapes, such as blunt or rounded. In an implementation, the tip of the laparoscopic tube is not transverse with respect to the lateral extent of the tube of the element. That is, the probe face of the sensor head is not transverse to the lateral extent of the tube of the element. In an implementation, source structures and detector structures are positioned along the sides of the laparoscopic tube so that the structures can make contact with target tissue when the tip cannot make contact with target tissue or such contact is difficult to make with the tip. In some embodiments, the sensor head is flush with the end of the laparoscopic tube, recessed within the laparoscopic tube, or extends from the laparoscopic tube.

Figure 11:
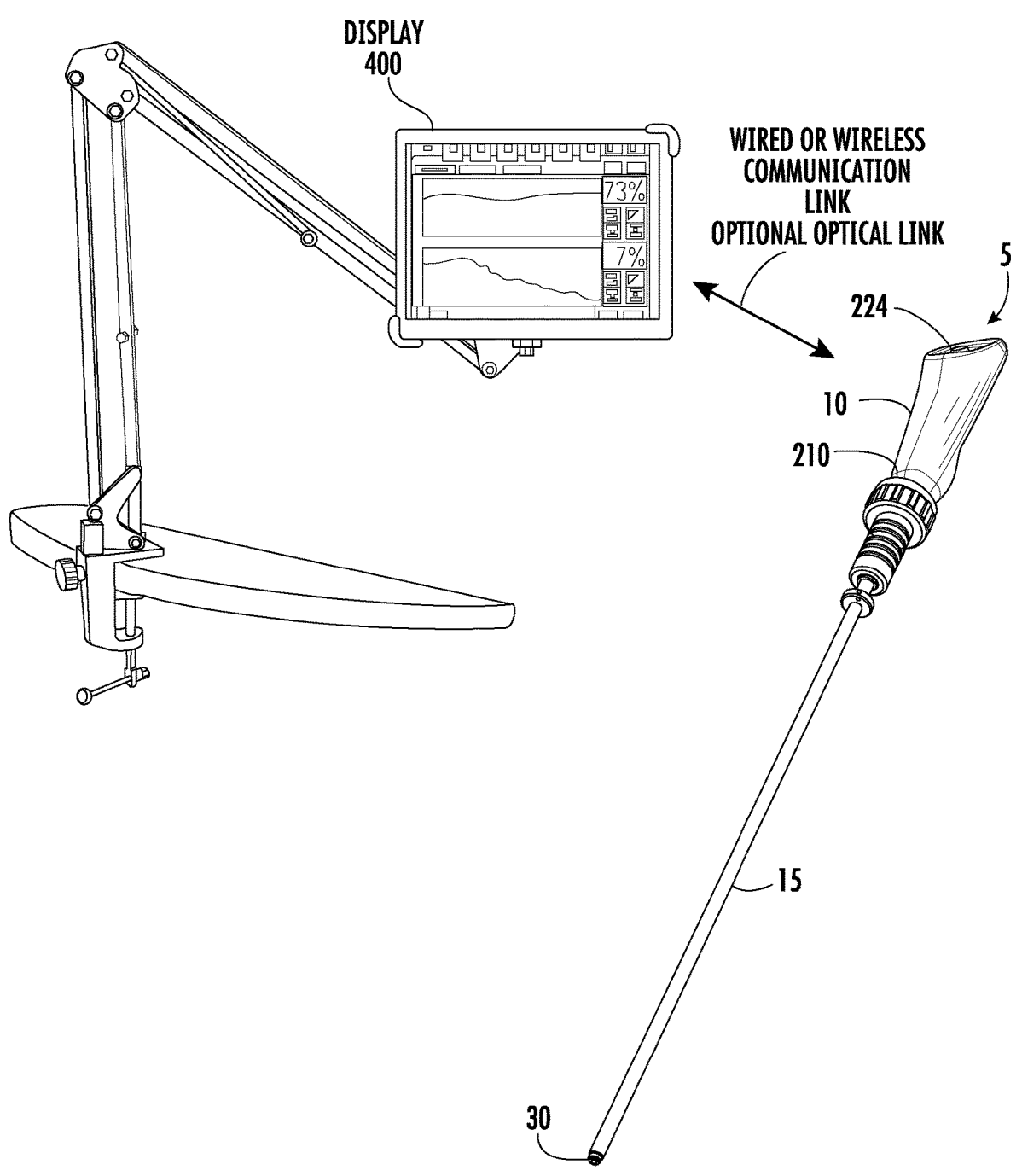
FIG. 11 shows an oximeter probe that is configured to transmit oximetry information to a display via a communication link for the display of the oximetry information on the display.

FIG. 11 shows an oximeter probe 5 that is configured to transmit oximetry information to a display 400 via a communication link for display of the oximetry information on the display. Display 400 may be the display of a surgical tower or a stand-alone display. Oximeter probe 5 may be configured to communicate with display 400 via a wireless link, a wired link (e.g., cable), or an optical link (e.g., optical fiber).

The communication link can operate according to one of a variety of protocols, such as one of the Bluetooth protocols (e.g., Bluetooth, Bluetooth SMART, Bluetooth Low Energy, others), one of the IEEE 802.11 protocols, ANT, 6LoWPAN, MyriaNed, EnOcean, Z-Wave, Wi-Fi, one of the IEEE 802.15.4 protocol, such as ZigBee, or others. These or other wireless protocols can be used by the oximeter probe to transfer data from the probe to the display at the measurement rate at which the processor accesses the digitized data from the ADCs, for example about 1 hertz to 3 hertz. Data transfer from the display to the device can be at similar rates.

The wireless link between the oximeter probe and the display is a direct wireless connection, in an implementation. That is, no intermediary transmitter circuits, receiver circuits, or transceiver circuits receive the wireless signal transmitted from the oximeter probe for subsequent retransmission of the wireless signal to the display. Similarly, no intermediary transmitter circuits, receiver circuits, or transceiver circuits receive the wireless signal transmitted from the display for subsequent retransmission of the wireless signal to the oximeter probe.

In an implementation where the oximeter probe is adapted to communicate with display 400 for the display of information for oxygen saturation measurements, the probe does not include a display. In this implementation, display 400 operates as the display for the probe. Alternatively, the oximeter probe may include display 224 and may be adapted to communicate with display 400 where the two displays may display the same, different, or complementary oximetry information.

Display 400 can be a tablet computer or other display type, such as a display that is included in a laparoscopic tower used with other laparoscopic devices used during a laparoscopic surgery. In an implementation where the display is a tablet computer, the display can be attached to a laparoscopic tower that might include other displays and other medical devices. The display can operate an Android mobile operating system or another operating system adapted for use with mobile devices.

Display 400 includes circuitry and a power supply unit that is adapted to supply power to the circuitry. The power supply unit can include circuitry that provides power from a battery of the display. Alternatively, the power supply unit be adapted to receive power from a power outlet (e.g., 120 volts, 220 volts, or other voltages) for powering the display.

The circuitry may be referred to as a processing circuit and can include one or more electrical components or circuits, such as a processor, microprocessor, microcontroller, a multi-core processor, application specific integrated circuit (ASIC), field programmable gate array (FPGA), multiplexers, standard cells, control logic (e.g., programmable logic, programmable logic device (PLD), CPLD, and others), memory, look-up tables, state machines, logic gates, digital signal processors (DSP), and others. In an implementation, the processing circuit performs operations in digital (e.g., Boolean logic). The circuitry can include one or more memories, such as a volatile memory (e.g., a RAM), a nonvolatile memory (e.g., a disk or FLASH), or other memory types.

The circuitry of the display performs the processing of signal data generated by the photodetectors, performs calculations, determines oxygen saturation and other oximeter measurements, and other processing operations to thereafter display oximeter information (e.g., oxygen saturation information) on the display panel. The circuitry of the display can perform dark subtraction on the signal data to generate oximeter information, such as oxygen saturation information.

Display 400 can store and operate one or more computer applications adapted for receiving measurement information for oximeter measurements generated by the oximeter probe. The display, via the application, can process the information (including, for example, using dark subtraction methods on the information) and display the information or a derivative of the information. For example, the oximeter probe can transmit information (e.g., a value) for blood oxygen saturation (StO2), the percentage of oxygenated hemoglobin (HbO2), the percentage of deoxygenated hemoglobin (Hb), the blood volume, the melanin concentration, quality metric information for a quality of an oximetry measurement, or other oximetry information. The display can display one or more pieces of information for these values, such as the values themselves or derivatives of the values.

Alternatively, the oximeter probe can transmit substantially raw measurement data in digital or analog form to the display. Substantially raw measurement data includes data that has not been processed by the processor or any preprocessors. The substantially raw measurement data can be analog detector responses generated by the detectors that may or may not be conditioned, amplified, or both. The substantially raw measurement data can be digitized detector responses that are digitized by the oximeter probe via the analog-to-digital converter 259 housed within the oximeter probe. The display, via the use of the application, can perform data processing (including, for example, using dark subtraction methods on the data) on the raw measurement data to generate final measurement information for the tissue, such as a value for blood oxygen saturation (StO2), a value for the percentage of oxygenated hemoglobin (HbO2), a value for the percentage of deoxygenated hemoglobin (Hb), blood volume, melanin concentration, or other value. The display, via the application, can display one or more pieces of the oximetry information.

Alternatively, the oximeter probe can transmit partially processed measurement data to the display. Partially processed data can include data for which one or more calibration corrections have been made for intensity difference of light emitted by the LEDs, inherent sensitivity differences of the photodetectors, diameters or diameter ratios d1/d2 of the transmit and receive waveguides, other processed information, or any combination of this information. The display, via the use of the application, can perform data processing on the partially processed data to generate final measurement information for the tissue, such as a value for blood oxygen saturation (StO2), a value for the percentage of oxygenated hemoglobin (HbO2), a value for the percentage of deoxygenated hemoglobin (Hb), blood volume, melanin concentration, or other value. The display, via the application, can display one or more pieces of the oximetry information.

The battery of the display can include one or more of a variety of battery types, such as one or more disposable batteries or one or more rechargeable batteries. Disposable batteries are discarded after their stored charge is expended. Some disposable battery chemistry technologies include alkaline, zinc carbon, or silver oxide. The battery has sufficient stored charge to allow use of the handheld device for several hours. In an implementation, the oximeter probe is a disposable probe.

In implementations where the battery is rechargeable, the battery can be recharged multiple times after the stored charge is expended. Some rechargeable battery chemistry technologies include nickel cadmium (NiCd), nickel metal hydride (NiMH), lithium ion (Li-ion), and zinc air. The battery can be recharged, for example, via an AC adapter with a cord that connects to the handheld unit. The circuitry in the display can include a recharger circuit (not shown).

Figure 12A:
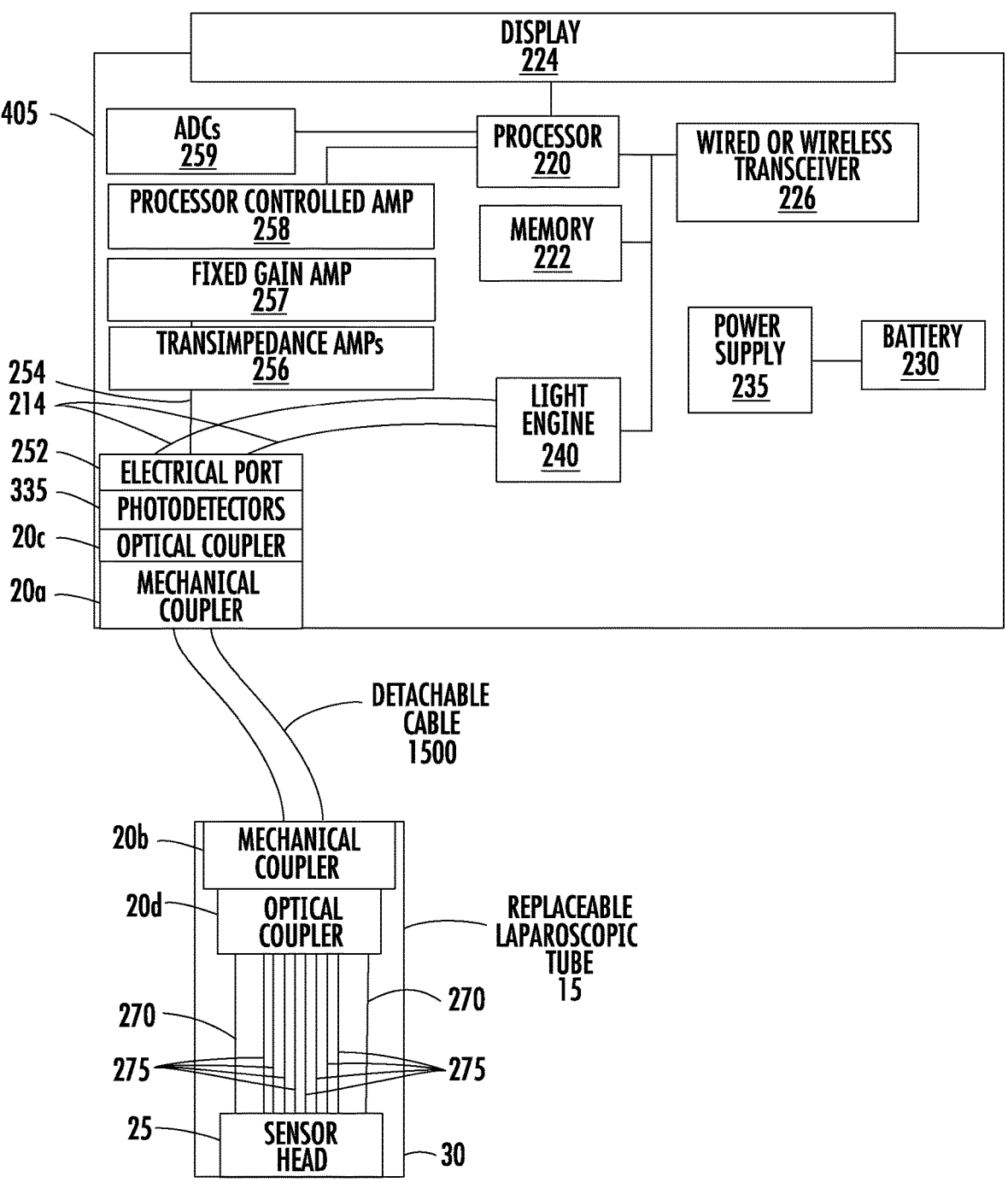
FIG. 12A shows a display that is connected to a replaceable laparoscopic tube by a detachable cable, in an implementation.

FIG. 12A shows a display 405 connected to a replaceable laparoscopic tube 15 by a detachable cable 1500, in an implementation. Display 405 includes the same or similar circuits and elements as probe unit 10 and upper laparoscopic tube 210, but differs from probe unit 10 in that the display includes mechanical coupler 20a and optical coupler 20c that connect to the detachable cable 1500. Specifically, the detachable cable is detachable from display 405 and detachable from replaceable laparoscopic tube 15. The detachable cable includes structures that detachably connect the cable to mechanical coupler 20a, optical coupler 20c, an electrical port 252, or any combination of the couplers and port. The detachable cable includes structures that detachably connect the cable to mechanical coupler 20b, optical coupler 20d, one of these couplers, or both of these couplers of the laparoscopic tube 15.

A first mechanical coupler of the cable can apply a spring force that connects the waveguides of the cable to the waveguides of the display. More specifically, the first mechanical coupler of the cable can apply a spring force that connects the waveguides of the cable to the waveguide ends located in optical coupler 20c. A second mechanical coupler of the cable can apply a spring force that connects the waveguides of the cable to the waveguides of the laparoscopic tube. More specifically, the second mechanical coupler of the cable can apply a spring force that connects the waveguides of the cable to the waveguide ends located in optical coupler 20d.

The cable can have a variety of lengths, such as 1 meter, 1.5 meters, 2 meters, or longer. The cable may be sufficiently long so that the display is located outside of the sterile field as will be understood by one of ordinary skill in the art. The cable can be relatively flexible, allowing the replaceable laparoscopic tube to be relatively freely moved for surgery.

With the cable connected to the display and laparoscopic tube, light generated by the light engine can be transmitted to the laparoscopic tube through the cable and reflected light that is reflected from tissue can be transmitted through the cable to the display. The light can be detected and converted to electrical signals by the photodetectors. The first and second mechanical couplers of the cable can each include one or two twist connectors, one or more a pin connectors, one or more aperture connectors, one or more key structures that guide the alignment of the cable onto the display or laparoscopic tube, other connector types, or one or more of these connectors in any combination.

The display can process the electrical signals (including, for example, using dark subtraction methods) to generate oximetry information, such as oxygen saturation information for tissue being measured. The display can display the oximetry information on the display element. The display element may have a diagonal length across the display of 5-100 centimeters.

Similar to the oximeter probe described above, the light engine of the display is electrically connected to the processor and the processor controls the generation of light by the light engine for emission of the light into tissue. The light engine includes one or more sources that generate and transmit light, such as visible light, infrared light, or both. Each source can include one or more light emitting diodes (LEDs), such as one, two, three, four, five, six, seven, eight, nine, ten, or more LEDs. Each LED is adapted to emit one or more wavelengths of light, such as visible light, infrared light, or both. The LEDs can be discrete LEDs, organic LEDs (OLEDs), high brightness LEDs (HLEDs), quantum dot LEDs, laser diodes, or other types of LEDs.

The LEDs of light engine 240 are optically connected to first ends of one or more waveguides 214, which are housed in the display. One, two, three, four, five, or more LEDs can be optically connected to one waveguide. Second ends of the waveguides are optically connected to optical coupler 20c.

The photodetectors of the display can be PIN photodiodes, phototransistors, photoresistors, or another detector type. The photodetectors can be connected to optical coupler 20c or another structure of the display, such as an aperture plate 330 shown in FIGS. 3A-3D. The display can include one or more transimpedance amplifiers (TIAs) 256 that are connected to the photodetectors. The photodetectors convert received light into electrical signals, which the TIAs amplify. Each photodetector may be electrically connected to one TIA. In an implementation, multiple photodetectors are connected to a single TIA, for example, via a multiplexer. The TIAs are adapted to receive analog detector responses generated by the photodetectors. The TIAs convert the current for the analog detector responses to a voltage and amplify the voltage.

The processor can monitor signals generated by the photodetectors simultaneously and generate multiple oximeter measurements, such as oxygen saturation measurements, at the same time (i.e., instantaneously).

In some implementations, the display includes one or more electrical components that perform these functions, such as one or more current-to-voltage converters and one or more voltage amplifiers. It will be understood that a TIA is one example of an electronic circuit that can perform the conversion and amplification.

The photodetectors may generate output current (e.g., detector responses) that changes relatively linearly with the changing intensity of detected light, whereas the generated output voltage changes relatively nonlinearly with the changing intensity of detected light. The TIA or current to voltage converter can output relatively linear voltage from the current to voltage conversion. Thereafter, the amplified voltage is also relatively linear.

The display can include one or more analog-to-digital converters 259. Similar to the probe unit described above, each TIA may be electrically connected to one ADC. In an implementation, multiple TIAs are connected to one ADC, for example, via a multiplexer. The ADCs are also electrically connected to the processor. The ADCs digitize the amplified voltage signal received from the TIAs and transfer the digitized detector responses to the processor.

The ADCs sample the analog signals at a sampling rate. For example, the sampling rate can be about on the order of kilohertz, such as about 200-300 kilohertz. The measurement rate that the processor operates on the digitized signals is less than the sampling rate. The measurement rate that the processor operates on the digitized signals is about 1-3 hertz (depending on the conditions of the oximeter probe). In other implementations, the measurement rate can be above 3 hertz, such as from about 4 hertz to about 1 kilohertz. Generally, the faster the sampling rate of the ADCs and the operating frequency of the processor, the more power that is consumed, which is a consideration for a battery-operated device, and also the data generated increases with the sample rate.

When using a measurement rate of about 0.33 to about 3 hertz, the amount of data can be transmitted wirelessly by the transceiver to other devices (e.g., a computer or a display) using technologies such as Bluetooth and Wi-Fi (and others mentioned in this patent) without data loss. In other implementations, a proprietary wireless technology can be used, such as when higher sampling rates are desired.

Figure 12B:
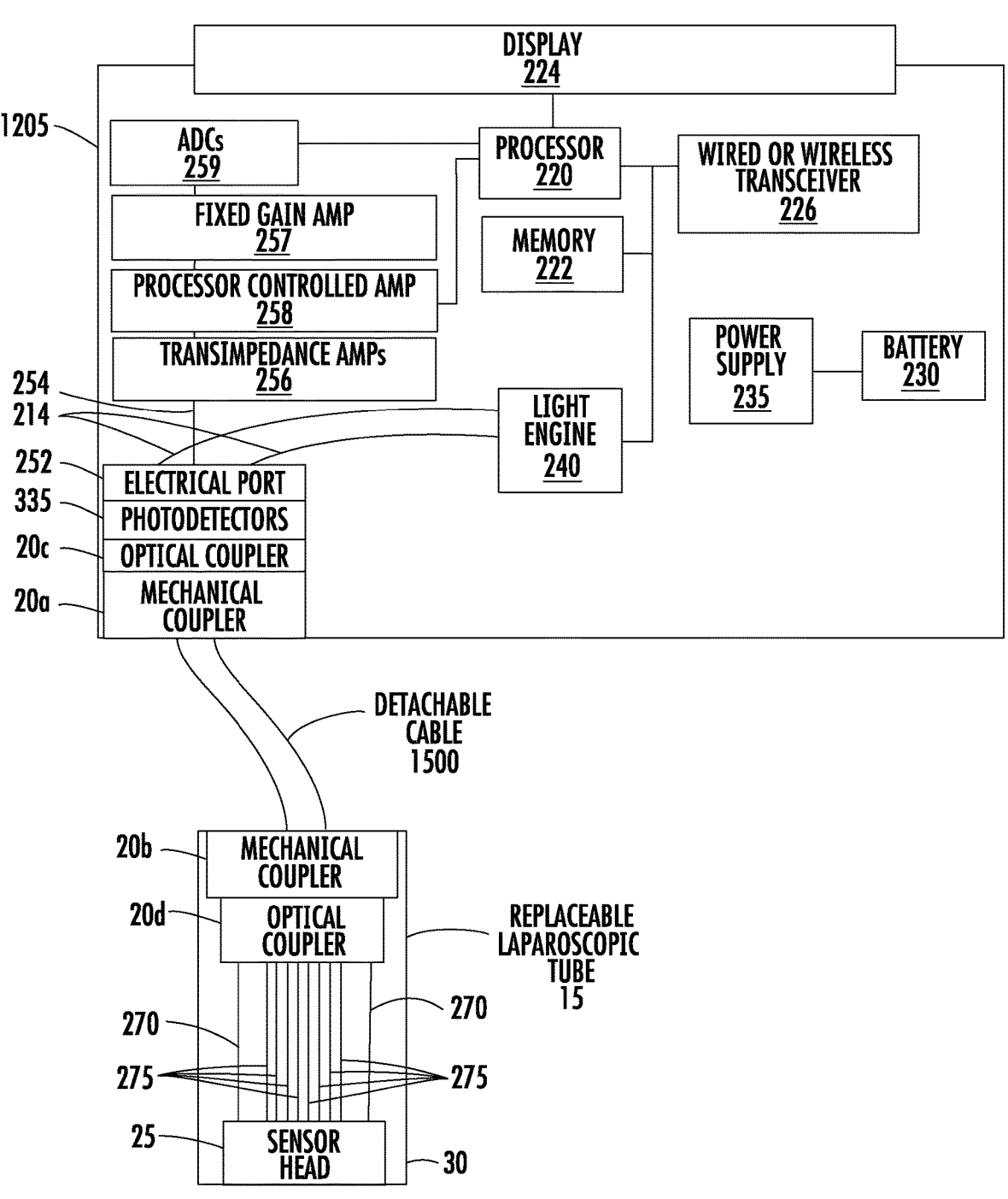
FIG. 12B shows a display connected to a replaceable laparoscopic tube by a detachable cable, in an implementation.

FIG. 12B shows a display 1205 connected to a replaceable laparoscopic tube 15 by a detachable cable 1500, in an implementation. Display 1205 is similar to display 405 but differs in that the processor-controlled amplifier 258 is connected to the fixed gain amplifier 257 and the transimpedance amplifier 256 and is connected between the fixed gain amplifier and the transimpedance amplifier.

Figure 12C:
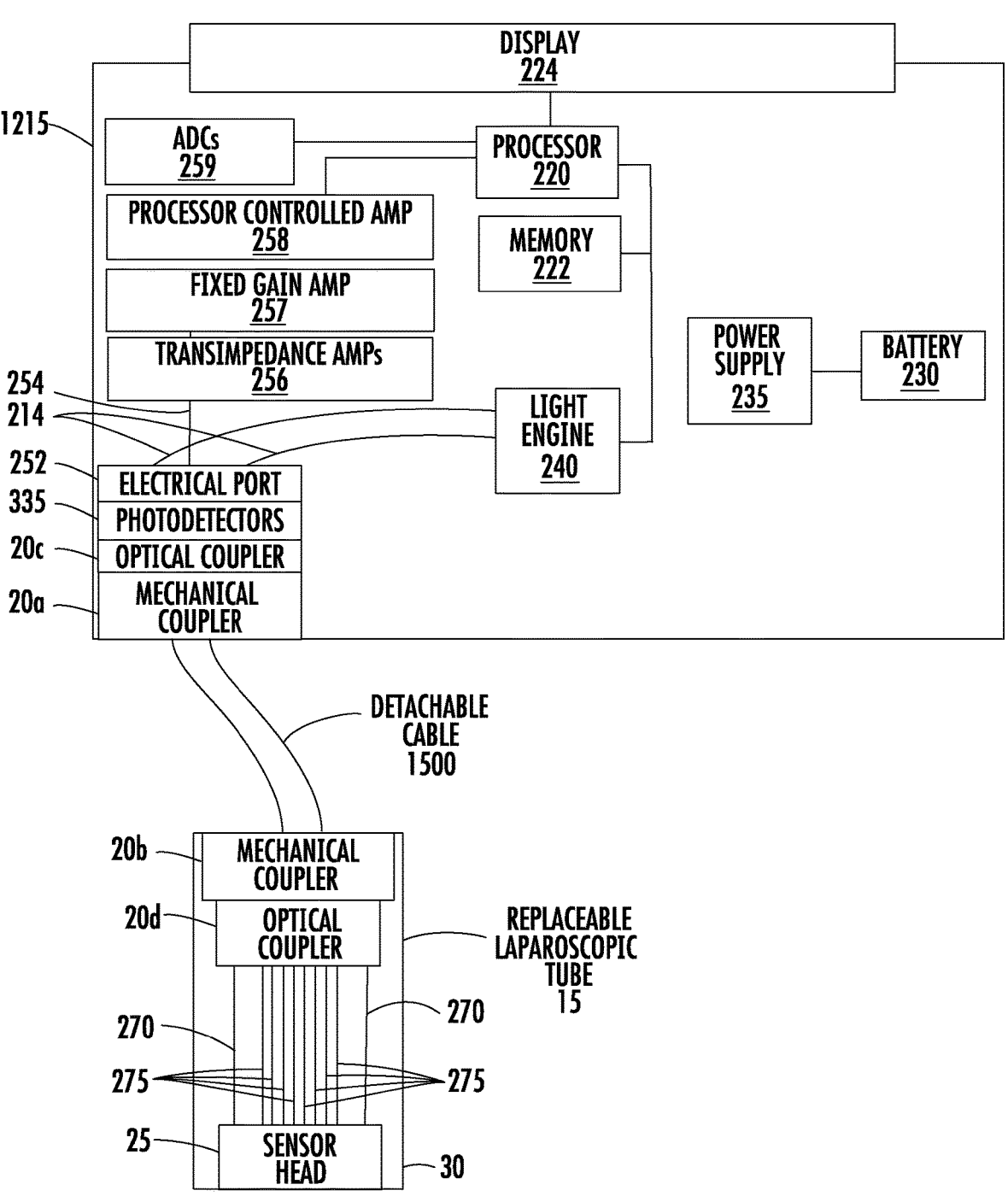
FIG. 12C shows a display connected to a replaceable laparoscopic tube by a detachable cable, in an implementation.

FIG. 12C shows a display 1215 connected to a replaceable laparoscopic tube 15 by a detachable cable 1500, in an implementation. Display 1215 is similar to display 405 shown in FIG. 12A but differs in that display 1215 does not include transceiver 226.

Figure 12D:
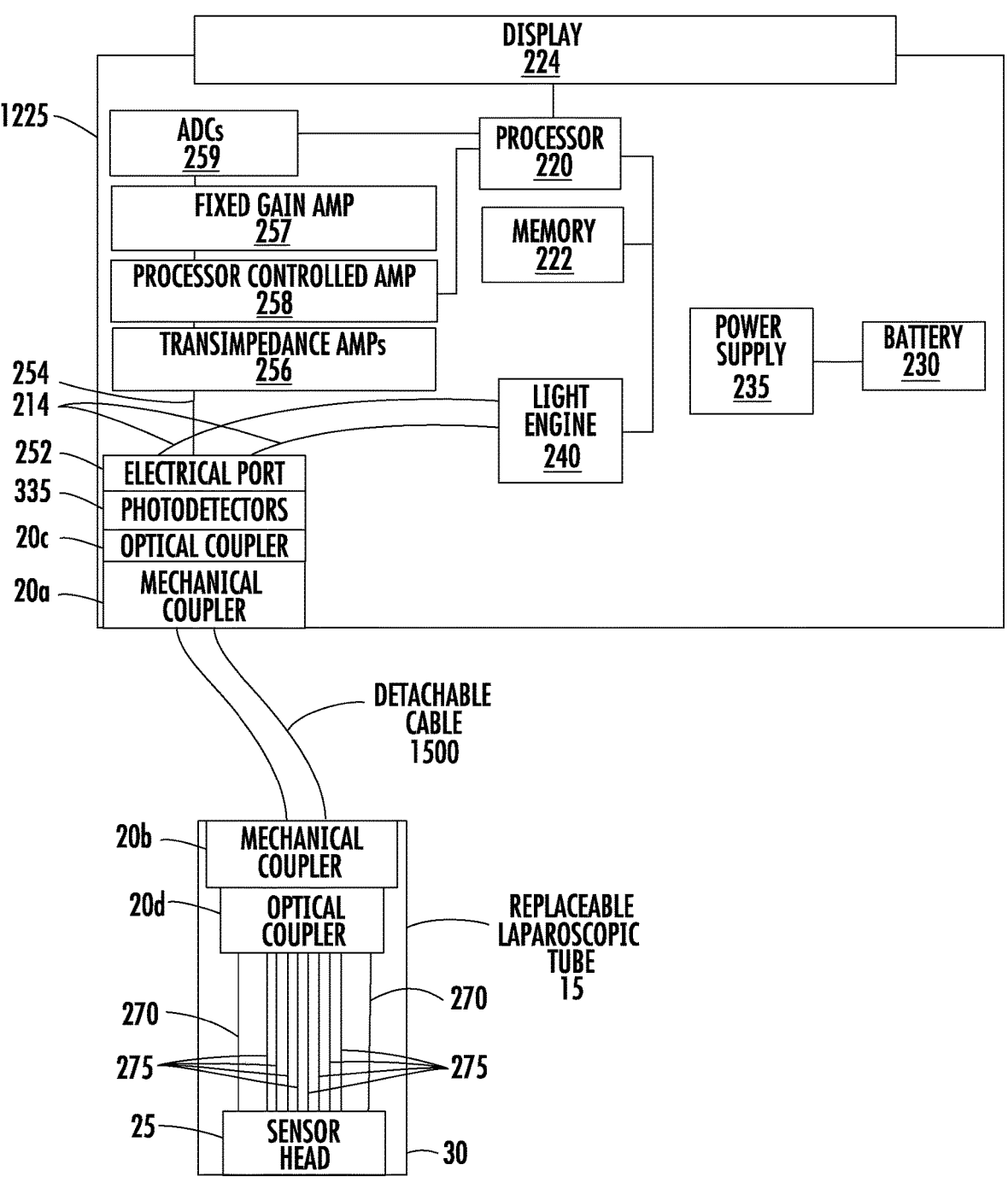
FIG. 12D shows a display connected to a replaceable laparoscopic tube by a detachable cable, in an implementation.

FIG. 12D shows a display 1225 connected to a replaceable laparoscopic tube 15 by a detachable cable 1500, in an implementation. Display 1215 is similar to display 1205 shown in FIG. 12B but differs in that display 1225 does not include transceiver 226.

This description of the invention has been presented for the purposes of illustration and description. It is not intended to be exhaustive or to limit the invention to the precise form described, and many modifications and variations are possible in light of the teaching above. Elements of the various implementations can be used with other implementations in a number of ways, such as combinations, substitutions, or both. The implementations were chosen and described in order to best explain the principles of the invention and its practical applications. This description will enable others skilled in the art to best utilize and practice the invention in various implementations and with various modifications as are suited to a particular use. The scope of the invention is defined by the following claims.

The invention claimed is:

1. A method comprising: forming a housing comprising a first structure and a second structure, wherein providing the housing is reusable and is configured for use with a plurality of first laparoscopic element elements that is disposable; forming a first opening at an end of the first structure portion; positioning in the first structure a processor, a memory coupled to the processor, and a light engine coupled to the processor; forming a second opening at a first end of the second structure; coupling the second structure to the first structure by coupling the second opening of the second structure to the first opening of the first structure, wherein the first opening comprises a through hole through which a first optical conductor passes, and the first optical conductor passes through a through hole of the second opening of the second structure; forming a first optical interface at a second end of the second structure; coupling the first optical conductor that has passed through the first and second openings to the light engine and the first optical interface; forming the first laparoscopic element to removably couple to the second structure of the housing and comprising a third structure, a fourth structure, and a second optical conductor; forming a third opening at a first end of the third structure and at a first end of the first laparoscopic element; forming a fourth opening in the third structure oppositely located from the third opening in the third structure; coupling an interior surface of the third structure over an outside surface of the second structure through the third opening forming a mated connection coupling when the laparoscopic element is removably coupled to the second structure of the housing; positioning a sensor head at a second end of the fourth structure that is oppositely located from a first end of the fourth structure; optically coupling the second optical conductor to the first optical conductor in an interior space of the third structure when the first laparoscopic element is removably coupled to the second structure of the housing; and coupling the second optical conductor through an interior space of the fourth structure to the sensor head, wherein at least a portion of the first structure is inserted through the through hole of the second opening of the second structure.

2. The method of claim 1 comprising forming a male portion of the second structure; and forming a female portion of the third structure, wherein coupling the interior surface of the third structure over the outside surface of the second structure through the third opening forming the mated connection coupling comprises positioning the male portion of the second structure in the female portion of the third structure.

3. The method of claim 1 wherein the third opening of the third structure comprises a first diameter, and the fourth opening of the third structure comprises a second diameter less than the first diameter.

4. The method of claim 1 comprising forming the fourth opening at a position closer to a tip of the first laparoscopic element than the first end of the first laparoscopic element.

5. The method of claim 1 comprising:
forming exterior threads on the second structure;
forming interior threads of the third structure; and
threading the exterior threads onto the interior threads to form the mated connection coupling when the housing and first laparoscopic element are removably coupled.

6. The method of claim 1 comprising providing the mated connection coupling is a latched connection coupling.

7. The method of claim 1 comprising providing the mated connection coupling is a spring-loaded connection coupling.

8. The method of claim 1 comprising coupling a display to the first structure visible from an exterior of the first structure.

9. The method of claim 1 comprising inserting the first end of the fourth structure in the interior space of the third structure through the fourth opening of the third structure when the housing and first laparoscopic element are removably coupled.

10. The method of claim 1 comprising providing the second optical conductor is longer than the first optical conductor.

11. The method of claim 1 comprising positioning the second optical conductor at least partially in an interior space of the fourth structure.

12. The method of claim 1 comprising end-to-end coupling the first and second optical conductors when the housing and first laparoscopic element are removably coupled.

13. The method of claim 1 comprising providing the second structure comprises a printed circuit board (PCB), a photodetector located on a surface of the PCB and coupled to the processor, and a third optical conductor coupled to the photodetector; and providing the first laparoscopic element comprises a
      fourth optical conductor optically coupled to the pho-
      todetector when the housing and laparoscopic element
      are removably coupled and coupled to the sensor head.

14. The method of claim 1 comprising providing the second optical conductor is at least twice as long as the first optical conductor.

15. The method of claim 1 wherein the coupling of the second structure to the first structure by coupling the second opening of the second structure to the first opening of the first structure comprises coupling the first and second structures in a fixed configuration.

16. The method of claim 1 wherein the first and second openings are coaxial.

17. The method of claim 1 comprising forming a second optical interface in the interior space of the third structure; and coupling the first and second optical interfaces in an interior space of the third structure.

18. The method of claim 1 wherein the second end of the second structure is oppositely located from the first end of the second structure.

19. The method of claim 1 wherein the housing comprising the first and second structures is configured for use with a second laparoscopic element that is disposable.

20. The method of claim 19 wherein the housing comprising the first and second structures is configured for use with the second laparoscopic element when the first laparoscopic element is detached from the housing.

21. The method of claim 13 comprising providing the fourth optical conductor is longer than the first optical conductor and the second optical conductor is longer than the third optical conductor.

22. The method of claim 21 comprising providing the fourth optical conductor is longer than the third optical conductor.

23. The method of claim 22 comprising configuring the surface of the PCB on which the photodetector is coupled to face away from the first laparoscopic element.

24. The method of claim 22 comprising providing the fourth optical conductor fiber is at least twice as long as the third optical conductor.

25. A method comprising: forming housing comprising a first structure and a second structure, wherein providing the housing is reusable and is configured for use with a plurality of first laparoscopic element elements that is disposable; forming a first opening at an end of the first structure, wherein the first opening comprises a through hole; positioning in the first structure a processor, a memory coupled to the processor, and a light engine coupled to the processor, coupling the second structure to the first structure by coupling a second opening of the second structure to the first opening of the first structure, wherein the second opening comprises a through hole through which at least a portion of the first structure is inserted through; coupling a first optical conductor through the through holes of the first and second openings to the light engine and a first optical interface; forming laparoscopic element, removably couplable to the second structure of the housing, comprising a third structure, a fourth structure, and a second optical conductor; forming a third opening in the third structure at a first end of the first laparoscopic element; forming a fourth opening in the third structure oppositely located from the third opening; coupling an interior surface of the third structure over an outside surface of the second structure through the third opening forming a mated connection coupling when the laparoscopic element is removably coupled to the second structure of the housing; positioning a sensor head at a second end of the fourth structure that is oppositely located from a first end of the fourth structure; optically coupling the second optical conductor to the first optical conductor in an interior space of the third structure when the laparoscopic element is removably coupled to the second structure of the housing; coupling the second optical conductor through an interior space of the fourth structure to the sensor head; positioning a printed circuit board (PCB) in the second structure; coupling a photodetector to a surface of the PCB and to the processor via the PCB; optically coupling a third optical conductor to the photodetector in the second structure; positioning a fourth optical conductor in the laparoscopic element; coupling the fourth optical conductor through the laparoscopic element to the sensor second head; and coupling the fourth optical conductor though the laparoscopic element to third optical conductor when the housing and laparoscopic element are removably coupled, wherein at least a portion of the first structure is inserted through the through hole of the second opening of the second structure.

26. The method of claim 25 comprising forming a male portion of the second structure; and forming a female portion of the third structure, wherein coupling the interior surface of the third structure over the outside surface of the second structure through the third opening forming the mated connection coupling comprises positioning the male portion of the second structure in the female portion of the third structure.

27. The method of claim 25 comprising providing the third opening of the third structure comprises a first diameter and the fourth opening of the third structure comprises a second diameter less than the first diameter.

28. The method of claim 25 comprising:
   forming exterior threads on the second structure;
   forming interior threads of the third structure; and
   threading the exterior threads onto the interior threads to
      form the mated connection coupling when the housing
      and laparoscopic element are removably coupled.

29. The method of claim 25 wherein the coupling of the second structure to the first structure by coupling the second opening of the second structure to the first opening of the first structure comprises coupling the first and second structures in a fixed configuration.

30. The method of claim 25 wherein the second end of the second structure is oppositely located from the first end of the second structure.

31. The method of claim 25 wherein the housing comprising the first and second structures is configured for use with a second laparoscopic element that is disposable.

32. The method of claim 31 wherein the housing comprising the first and second structures is configured for use with the second laparoscopic element when the first laparoscopic element is detached from the housing.

* * * * *